US012773128B2

(12) United States Patent
Bodurka et al.

(10) Patent No.: US 12,773,128 B2
(45) Date of Patent: Oct. 27, 2026

(54) PATIENT SUPPORT APPARATUSES WITH HEADWALL COMMUNICATION

(71) Applicant: Stryker Corporation, Kalamazoo, MI (US)

(72) Inventors: Alexander Josef Bodurka, Portage, MI (US); Jerald A. Trepanier, Augusta, MI (US); Thomas Deeds, Seattle, WA (US); Madhu Sandeep Thota, Portage, MI (US); Placide Nibakuze, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 987 days.

(21) Appl. No.: 17/913,714

(22) PCT Filed: May 14, 2021

(86) PCT No.: PCT/US2021/032426

§ 371 (c)(1),
(2) Date: Sep. 22, 2022

(87) PCT Pub. No.: WO2021/236437

PCT Pub. Date: Nov. 25, 2021

(65) Prior Publication Data

US 2023/0110653 A1 Apr. 13, 2023

Related U.S. Application Data

(60) Provisional application No. 63/026,937, filed on May 19, 2020.

(51) Int. Cl.
*A61B 5/11* (2006.01)
*A61B 5/00* (2006.01)

(52) U.S. Cl.
CPC .......... *A61B 5/1115* (2013.01); *A61B 5/6891* (2013.01)

(58) Field of Classification Search
CPC ... A61B 5/1115; A61B 5/6891; A61G 7/0506; A61G 7/0524; A61G 5/746; A61G 7/05; G16H 40/20; G16H 40/67; A47C 21/04
See application file for complete search history.

(56) References Cited

U.S. PATENT DOCUMENTS 8,334,777 B2 12/2012 Wilson et al.
8,917,166 B2 12/2014 Collins, Jr. et al.
(Continued)

FOREIGN PATENT DOCUMENTS

EP 4153050 A4 7/2024
WO WO9427544 A2 12/1994
WO WO2021046171 A1 3/2021

OTHER PUBLICATIONS

PCT International Written Opinion dated Augutst 18, 2021, for International application No. PCT/US2021/032426.
(Continued)

*Primary Examiner* — Matthew Troutman
*Assistant Examiner* — Alison N Labarge
(74) *Attorney, Agent, or Firm* — Gardner, Linn, Burkhart & Ondersma LLP

(57) ABSTRACT

A patient support apparatus includes a frame, support surface, first and second wireless transceivers, a room control, and a controller. The first transceiver communicates with a headwall module and the second transceiver communicates with a local area network. The room control controls a feature of a room device. The controller transmits a room control signal to the headwall module via the first transceiver in response to a user activating the room control on the patient support apparatus, and receives a room control command from an off-board source via the second wireless transceiver. The controller also transmits the room control signal to the headwall module via the first transceiver in response to receiving the room control command. The
(Continued)

headwall module forwards the room control signal to the room device, thereby allowing the room device to be controlled both by the room control and by the off-board source.

16 Claims, 14 Drawing Sheets

(56) References Cited

U.S. PATENT DOCUMENTS

| | | | | |
|---|---|---|---|---|
| 10,085,905 | B2 | 10/2018 | Bhimavarapu et al. | |
| 10,235,845 | B2 | 3/2019 | Bhimavarapu et al. | |
| 10,339,911 | B2 | 7/2019 | Bhimavarapu et al. | |
| 2002/0014951 | A1 * | 2/2002 | Kramer | G16H 10/60 340/286.07 |
| 2007/0210917 | A1 * | 9/2007 | Collins, Jr. | G08B 5/222 340/539.1 |
| 2013/0318716 | A1 * | 12/2013 | Vanderpohl, III | G06F 3/14 5/600 |
| 2016/0038361 | A1 * | 2/2016 | Hayes | H04B 10/1149 |
| 2016/0367415 | A1 | 12/2016 | Hayes et al. | |
| 2018/0293849 | A1 * | 10/2018 | Bhimavarapu | A61B 5/7475 |
| 2018/0344254 | A1 | 12/2018 | George et al. | |
| 2019/0008709 | A1 | 1/2019 | Bhimavarapu et al. | |
| 2019/0046379 | A1 | 2/2019 | Constant et al. | |
| 2019/0159948 | A1 | 5/2019 | Kostic | |
| 2019/0183705 | A1 | 6/2019 | Bodurka | |
| 2020/0050750 | A1 * | 2/2020 | Heil | G16H 10/60 |
| 2020/0051405 | A1 | 2/2020 | Bhimavarapu | |
| 2020/0327784 | A1 | 10/2020 | Bodurka et al. | |
| 2020/0337470 | A1 * | 10/2020 | Sayadi | A47C 21/04 |

OTHER PUBLICATIONS

Australian Examination Report 1 for Application No. 2021277184, dated Jun. 27, 2025, an AU counterpart to U.S. Appl. No. 17/913,714.

Supplementary European Search Report for Application No. 21809413.4, dated Jun. 7, 2024, an EP counterpart to U.S. Appl. No. 17/913,714.

* cited by examiner

| | |
|---|---|
| Pin 1 | Bed Monitoring Status On |
| Pin 2 | Read Light |
| Pin 3 | Room Light |
| Pin 4 | Speaker High |
| Pin 5 | Potentiometer Wiper |
| Pin 6 | Bed Exit Status On |
| Pin 7 | Nurse Call Interlock |
| Pin 8 | Audio Transfer - |
| Pin 9 | Audio Transfer + |
| Pin 10 | Interlock + |
| Pin 11 | Interlock - |
| Pin 12 | Bed Monitoring Fowler 30 deg. Alert |
| Pin 13 | No Connect |
| Pin 14 | Potentiometer Low Common |
| Pin 15 | Potentiometer High Common (Std.) / Audio (STV) |
| Pin 16 | Nurse Answer Light + |
| Pin 17 | Bed Monitor Alert |
| Pin 18 | Bed Monitoring Siderail Alert |
| Pin 19 | Nurse Call Light + |
| Pin 20 | No Connect |
| Pin 21 | No Connect |
| Pin 22 | No Connect |
| Pin 23 | Brake Status On |
| Pin 24 | No Connect |
| Pin 25 | Nurse Call + |
| Pin 26 | Nurse Call NO/NC |
| Pin 27 | Room/Read Light Common |
| Pin 28 | Nurse Call Light - |
| Pin 29 | Nurse Answer Light - |
| Pin 30 | Priority NO/NC |
| Pin 31 | Priority Common |
| Pin 32 | Bed Monitoring Low Height Alert |
| Pin 33 | TV - (Std.) / Data (STV) |
| Pin 34 | TV + (Std.) / Common (STV) |
| Pin 35 | Speaker Low Common |
| Pin 36 | Audio Shield |
| Pin 37 | Bed Monitoring Common |

FIG. 18
(Prior Art)

PATIENT SUPPORT APPARATUSES WITH HEADWALL COMMUNICATION

BACKGROUND

The present disclosure relates to patient support apparatuses, such as beds, cots, stretchers, recliners, or the like. More specifically, the present disclosure relates to patient support apparatuses that are adapted to communicate with an existing nurse call system and/or one or more room devices.

Existing hospital beds often include an exit detection system that detects when the patient leaves the bed and notifies a nurse call system that the patient has left the bed. Existing hospital beds also often include a nurse call button and speaker that allow the patient to communicate with a remote nurse using the nurse call system. Still other signals of the bed may also be communicated to and/or through the nurse call system, and/or to a room interface that routes the signals to one or more room devices. Such room devices may include a television, one or more lights, a thermostat, etc., and the signals communicated from the bed may include commands to change one or features of these devices (e.g. a volume or channel of the television, an on/off state of the television, a room temperature, etc.)

In order for the bed to communicate this information to the nurse call system or the room devices, the bed must be configured in a manner that corresponds to the particular nurse call system and room devices that have been installed in a particular healthcare facility, or a particular room of the healthcare facility. This is because different manufacturers of nurse call systems and room devices handle communications in different manners. Further, communication between the bed and these devices is typically carried out via a cable running from the bed to a communications outlet mounted in a headwall of the room, and the structure and/or configuration of the communications outlet may vary from room to room and/or from healthcare facility to healthcare facility.

SUMMARY

According to various embodiments, the present disclosure provides one or more improved features for expediting and/or reducing the labor associated with configuring a patient support apparatus to communicate with one or more room devices, and/or for remotely controlling one or more room devices via the patient support apparatus. In some embodiments, a patient support apparatus is used as a communication conduit for controlling and/or configuring such room devices, which may include a television, a room light, a reading light, a headwall module, and/or a thermostat. In some aspects, the patient support apparatus may adapted to receive a schedule for controlling the one or more room devices, wherein the schedule is time based and/or event based. In some embodiments, the patient support apparatus forwards the schedule to a headwall interface that utilizes the schedule to control the room device(s), while in other embodiments, the patient support apparatus retains the schedule in its memory and uses the schedule to control the room devices itself.

According to a first embodiment of the present disclosure, a patient support apparatus is provided that includes a frame, a support surface for supporting a patient thereon, a first wireless transceiver, a second wireless transceiver, a room control, and a controller. The first wireless transceiver is adapted to communicate with a headwall module attached to a headwall of a healthcare facility at a fixed location. The headwall module is adapted to be electrically coupled to an outlet on the headwall and includes at least one pin in electrical communication with a room device positioned within a room in which the patient support apparatus is located. The second wireless transceiver is adapted to communicate with a server hosted on a local area network of the healthcare facility. The second wireless transceiver is adapted to communicate with the server via a wireless access point of the local area network. The room control is adapted to be activated by the patient and to control a feature of the room device in response to such activation. The controller is adapted to transmit a room control signal to the headwall module via the first wireless transceiver in response to a user activating the room control on the patient support apparatus. The controller is further adapted to receive a room control command from an off-board source via the second wireless transceiver and to transmit the room control signal to the headwall module via the first wireless transceiver in response to receiving the room control command. The headwall module is adapted to forward the room control signal to the room device to thereby allow the room device to be controlled both by the room control and by the off-board source.

According to other aspects of the present disclosure, the room device is a room light positioned in the room and the feature of the room device is an on/off state of the room light.

In some embodiments, the room device is a television positioned in the room and the feature of the room device is at least one of a channel or a volume of the television.

In some embodiments, the controller is further adapted to receive a room control schedule from the off-board source and to use the room control schedule to automatically control the feature of the room device according to the room control schedule. In such embodiments, the controller is either configured to forward the room control schedule to the headwall module via the first wireless transceiver and to instruct the headwall module to send control signals to the room device according to the room control schedule, or the controller is configured to retain the room control schedule and send control signals to the headwall module according to the room control schedule.

The controller of the patient support apparatus, in some embodiments, is configured to receive room configuration data from the off-board source via the second wireless transceiver. The room configuration data includes voltage data specifying a voltage level to apply to the pin in order to control the television. The room configuration data may additionally, or alternatively, include sequence data specifying a first sequence of voltage levels to apply to the pin to cause the television to change channels and/or a second sequence of voltage levels to apply to the pin to cause the television to change volume.

The controller is further configured, in some embodiments, to forward the room configuration data to the headwall module via the first wireless transceiver and to instruct the headwall module to use the room configuration data for controlling voltages applied to the pin.

In some embodiments, the patient support apparatus further comprises an exit detection system adapted to detect when the patient exits from the support surface and to issue an exit alert in response thereto. In such embodiments, the outlet further includes multiple pins in communication with a nurse call system and the controller is further adapted to receive nurse call configuration data from the off- board source via the second wireless transceiver and to forward the nurse call configuration data to the headwall module via the first wireless transceiver. The nurse call configuration data indicates which pin of the multiple pins is to be used to communicate the exit alert to the nurse call system.

In some embodiments, the first wireless transceiver is a Bluetooth transceiver and the second wireless transceiver is a WiFi transceiver.

In some embodiments, the off-board source is a one of a smart phone, a tablet computer, or a laptop computer in communication with the server.

The patient support apparatus, in some embodiments, further comprises a headwall interface adapted to couple to a cable having a plurality of electrical conductors wherein a first one of the electrical conductors is adapted to be in electrical communication with the pin when a cable is coupled to the outlet instead of the headwall module. The controller is further adapted to automatically retrieve from the headwall module room configuration data that specifies a voltage level to apply to the pin in order to control the television. The controller is further adapted to use the voltage data to control the television when the cable is coupled to the outlet and the patient activates the room control.

According to another aspect of the present disclosure, a patient support apparatus is provided that includes a frame, a support surface adapted to support a patient thereon, a first wireless transceiver, a second wireless transceiver, a room control, and a controller. The first wireless transceiver is adapted to communicate with a headwall module attached to a headwall of a healthcare facility at a fixed location. The headwall module is adapted to be electrically coupled to an outlet on the headwall, wherein the outlet includes at least one pin in electrical communication with a room device positioned within a room in which the patient support apparatus is located. The second wireless transceiver is adapted to communicate with a server hosted on a local area network of the healthcare facility. The second wireless transceiver is adapted to communicate with the server via a wireless access point of the local area network. The room control is adapted to control a feature of the room device in response to activation by the patient. The controller is adapted to transmit a room control signal to the headwall module via the first wireless transceiver in response to a user activating the room control on the patient support apparatus. The controller is further adapted to receive a room control schedule from an off-board source via the second wireless transceiver and to use the room control schedule to automatically control the feature of the room device according to the room control schedule.

In some embodiments, the room device is a room light positioned in the room and the feature of the room device is an on/off state of the room light. In such embodiments, the room control schedule includes at least one of automatically turning on or off the room light at a specified time.

In some embodiments, the room device is a television positioned in the room and the feature of the room device is at least one of a channel or a volume of the television. In such embodiments, the room control schedule includes at least one of turning off the television at a specified time or limiting a volume of the television at a specified time.

The controller of the patient support apparatus, in some embodiments, is adapted to use the room control schedule to override the room control such that, if the user activates the room control in a manner that conflicts with the room control schedule, the controller does not transmit the room control signal to the headwall module via the first wireless transceiver in response to the user activating the room control.

The controller of the patient support apparatus, in some embodiments, is configured to forward the room control schedule to the headwall module via the first wireless transceiver and to instruct the headwall module to send control signals to the room device according to the room control schedule. In other embodiments, the controller is adapted to retain the room control schedule and to send control signals to the headwall module according to the room control schedule.

In some embodiments, the controller is configured to receive room configuration data from the off-board source via the second wireless transceiver. The room configuration data includes voltage data specifying a voltage level to apply to the pin in order to control the television. The configuration data may also, or alternatively, include sequence data specifying a first sequence of voltage levels to apply to the pin to cause the television to change channels and/or a second sequence of voltage levels to apply to the pin to cause the television to change volume.

The controller is further configured, in some embodiments, to forward the room configuration data to the headwall module via the first wireless transceiver and to instruct the headwall module to use the room configuration data for controlling voltages applied to the pin.

In some embodiments, the patient support apparatus further comprises an exit detection system adapted to detect when the patient exits from the support surface and to issue an exit alert in response thereto. In such embodiments, the outlet further includes multiple pins in communication with a nurse call system and the controller is further adapted to receive nurse call configuration data from the off- board source via the second wireless transceiver and to forward the nurse call configuration data to the headwall module via the first wireless transceiver. The nurse call configuration data indicates which pin of the multiple pins is to be used to communicate the exit alert to the nurse call system.

The patient support apparatus, in some embodiments, further comprises a headwall interface adapted to couple to a cable having a plurality of electrical conductors wherein a first one of the electrical conductors is adapted to be in electrical communication with the pin when a cable is coupled to the outlet instead of the headwall module. The controller is further adapted to automatically retrieve from the headwall module room configuration data that specifies a voltage level to apply to the pin in order to control the television. The controller is further adapted to use the voltage data to control the television when the cable is coupled to the outlet and the patient activates the room control.

Still further, in some embodiments, the controller is further adapted to receive a room control command from the off-board source via the second wireless transceiver and to transmit the room control signal to the headwall module via the first wireless transceiver in response to receiving the room control command. In such embodiments, the headwall module is adapted to forward the room control signal to the room device to thereby allow the room device to be controlled both by the room control and by the off-board source.

According to still another embodiment of the present disclosure, a patient support apparatus is provided that includes a frame, a support surface adapted to support a patient thereon, a first wireless transceiver, a second wireless transceiver, a room control, and a controller. The first wireless transceiver is adapted to communicate with a headwall module attached to a headwall of a healthcare facility at a fixed location. The headwall module is adapted to be electrically coupled to an outlet on the headwall, wherein the outlet includes at least one pin in electrical communication with a room device positioned within a room in which the patient support apparatus is located. The second wireless transceiver is adapted to communicate with a server hosted on a local area network of the healthcare facility. The second wireless transceiver is adapted to communicate with the server via a wireless access point of the local area network. The room control is adapted to control a feature of the room device in response to being activated by the patient. The controller is adapted to transmit a room control signal to the headwall module via the first wireless transceiver in response to a user activating the room control on the patient support apparatus. The controller is further adapted to receive room configuration data from an off-board source via the second wireless transceiver. The room configuration data includes voltage data specifying a voltage level the headwall module is to apply to the pin in order to control the room device. The controller is adapted to forward the room configuration data to the headwall module via the first wireless transceiver and instruct the headwall module to use the room configuration data to control the voltage level applied to the pin when controlling the feature of the room device.

In some embodiments, the room device is a television positioned in the room and the feature of the room device is at least one of a channel or a volume of the television. In such embodiments, the room configuration data may further includes sequence data specifying a first sequence of voltage levels to apply to the pin cause the television to change channels and/or a second sequence of voltage levels to apply to the pin to cause the television to change volume.

In some embodiments, the patient support apparatus includes multiple room controls for controlling multiple room devices, and at least one of the room devices is a room light positioned in the room and the feature of the room device is an on/off state of the room light. Another one of the room devices may include a television.

In some embodiments, the patient support apparatus further comprises an exit detection system adapted to detect when the patient exits from the support surface and to issue an exit alert in response thereto. In such embodiments, the outlet further includes multiple pins in communication with a nurse call system and the controller is further adapted to receive nurse call configuration data from the off- board source via the second wireless transceiver and to forward the nurse call configuration data to the headwall module via the first wireless transceiver. The nurse call configuration data indicates which pin of the multiple pins is to be used to communicate the exit alert to the nurse call system.

The patient support apparatus, in some embodiments, further comprises a headwall interface adapted to couple to a cable having a plurality of electrical conductors wherein a first one of the electrical conductors is adapted to be in electrical communication with the pin when a cable is coupled to the outlet instead of the headwall module. The controller is further adapted to automatically retrieve from the headwall module room configuration data that specifies a voltage level to apply to the pin in order to control the television. The controller is further adapted to use the voltage data to control the television when the cable is coupled to the outlet and the patient activates the room control.

Still further, in some embodiments, the controller is further adapted to receive a room control command from the off-board source via the second wireless transceiver and to transmit the room control signal to the headwall module via the first wireless transceiver in response to receiving the room control command. In such embodiments, the headwall module is adapted to forward the room control signal to the room device to thereby allow the room device to be controlled both by the room control and by the off-board source.

The controller of the patient support apparatus, in some embodiments, is further adapted to receive a room control schedule from the off-board source and to use the room control schedule to automatically control the feature of the room device according to the room control schedule. In such embodiments, the controller may be adapted to forward the room control schedule to the headwall module via the first wireless transceiver and to instruct the headwall module to send control signals to the room device according to the room control schedule, or the controller may be adapted to retain the room control schedule and send control signals to the headwall module according to the room control schedule.

In any of the embodiments disclosed herein, the patient support apparatus may be one of a bed, a stretcher, a chair, a recliner, or a cot.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 18 is a chart of a prior art example of the functions of the pins of a 37-pin cable often used in existing healthcare facilities.

DETAILED DESCRIPTION OF THE EMBODIMENTS

Figure 1:
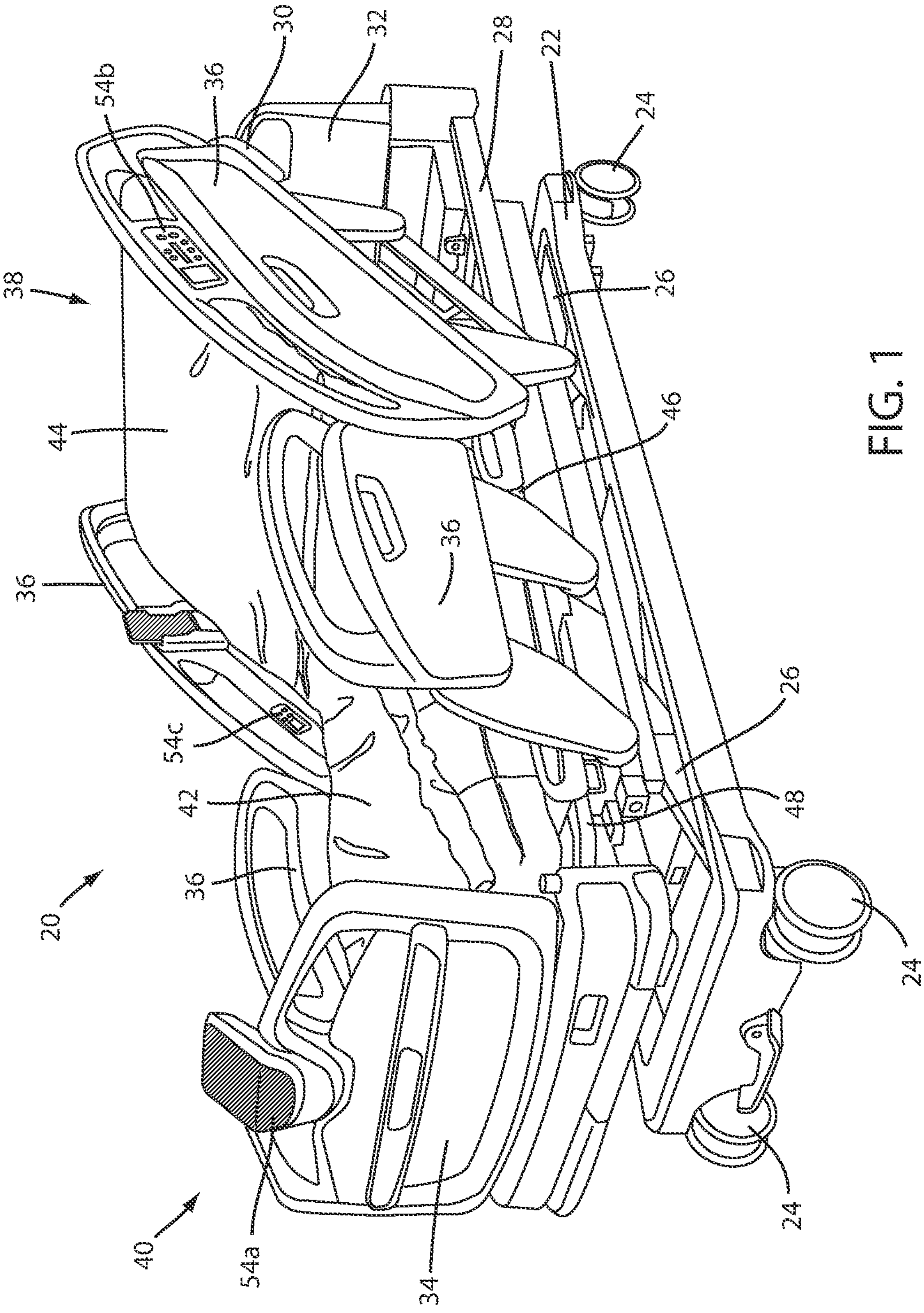
FIG. 1 is a perspective view of a patient support apparatus according to a first embodiment of the present disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. The top surface of the mattress 42 or other cushion forms a support surface for the occupant.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions, such as, but not limited to, that described in commonly assigned, U.S. Patent No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may be the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 20 can be designed with still other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on still other forms different from what is disclosed in the aforementioned references.

Figure 2:
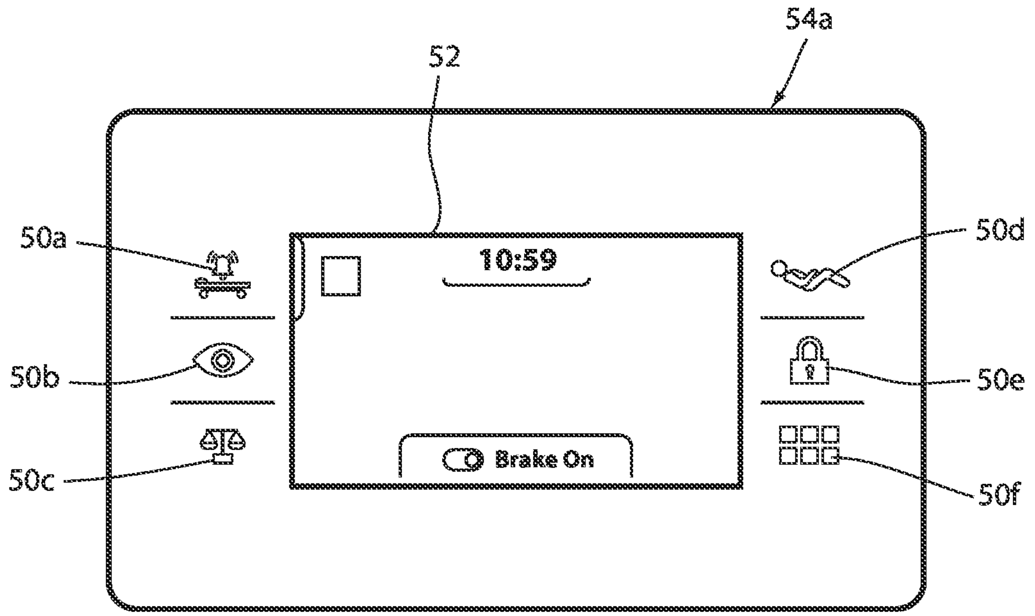
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54*a*, a pair of outer siderail control panels 54*b* (only one of which is visible), and a pair of inner siderail control panels 54*c* (only one of which is visible). Footboard control panel 54*a* and outer siderail control panels 54*b* are intended to be used by caregivers, or other authorized personnel, while inner siderail control panels 54*c* are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54*a* allow a user to control one or more of the following: change a height of support deck 30, raise or lower head section 44, activate and deactivate a brake for wheels 24, arm and disarm an exit detection system and, as will be explained in greater detail below, communicate with the particular IT infrastructure installed in the healthcare facility in which patient support apparatus 20 is positioned. One or both of the inner siderail control panels 54*c* also include at least one control that enables a patient to call a remotely located nurse (or other caregiver). In addition to the nurse call control, one or both of the inner siderail control panels 54*c* also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54*c* include, but are not limited to, the volume, the channel, the closed-captioning, and/or the power state of the television. With respect to the room and/or night lights, the features that may be controlled by one or more controls 50 on control panel 54*c* include the on/off state and/or the brightness level of these lights.

Control panel 54*a* includes a display 52 (FIG. 2) configured to display a plurality of different screens thereon. Surrounding display 52 are a plurality of navigation controls 50*a-f* that, when activated, cause the display 52 to display different screens on display 52. More specifically, when a user presses navigation control 50*a*, control panel 54*a* displays an exit detection control screen on display 52 that includes one or more icons that, when touched, control an onboard exit detection system. The exit detection system is as adapted to issue an alert when a patient exit from patient support apparatus 20. Such an exit detection system may include any of the features and functions as, and/or may be constructed in any of the same manners as, the exit detection system disclosed in commonly assigned U.S. patent application No. 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference.

When a user pressed navigation control 50*b* (FIG. 2), control panel 54 displays a monitoring control screen that includes a plurality of control icons that, when touched, control an onboard monitoring system built into patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses navigation control 50*c*, control panel 54*a* displays a scale control screen that includes a plurality of control icons that, when touched, control the scale system of patient support apparatus 20. Such a scale system may include any of the features and functions as, and/or may be constructed in any of the same manners as, the scale systems disclosed in commonly assigned U.S. patent application No. 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference.

When a user presses navigation control 50*d*, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50d may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

When a user presses navigation control 50*e*, control panel 54*a* displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses on navigation control 50*f*, control panel 54*a* displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

For all of the navigation controls 50*a-f* (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50*a-f*. It will also be understood that, although navigation controls 50*a-f* have all been illustrated in the accompanying drawings as dedicated controls that are positioned adjacent display 52, any one or more of these controls 50*a-f* controls alternatively be touchscreen controls that are displayed at one or more locations on display 52. Still further, although controls 50*a-f* have been shown herein as buttons, it will be understood that any of controls 50*a-f* could also, or alternatively, be switches, dials, or other types of non-button controls.

Figure 3:
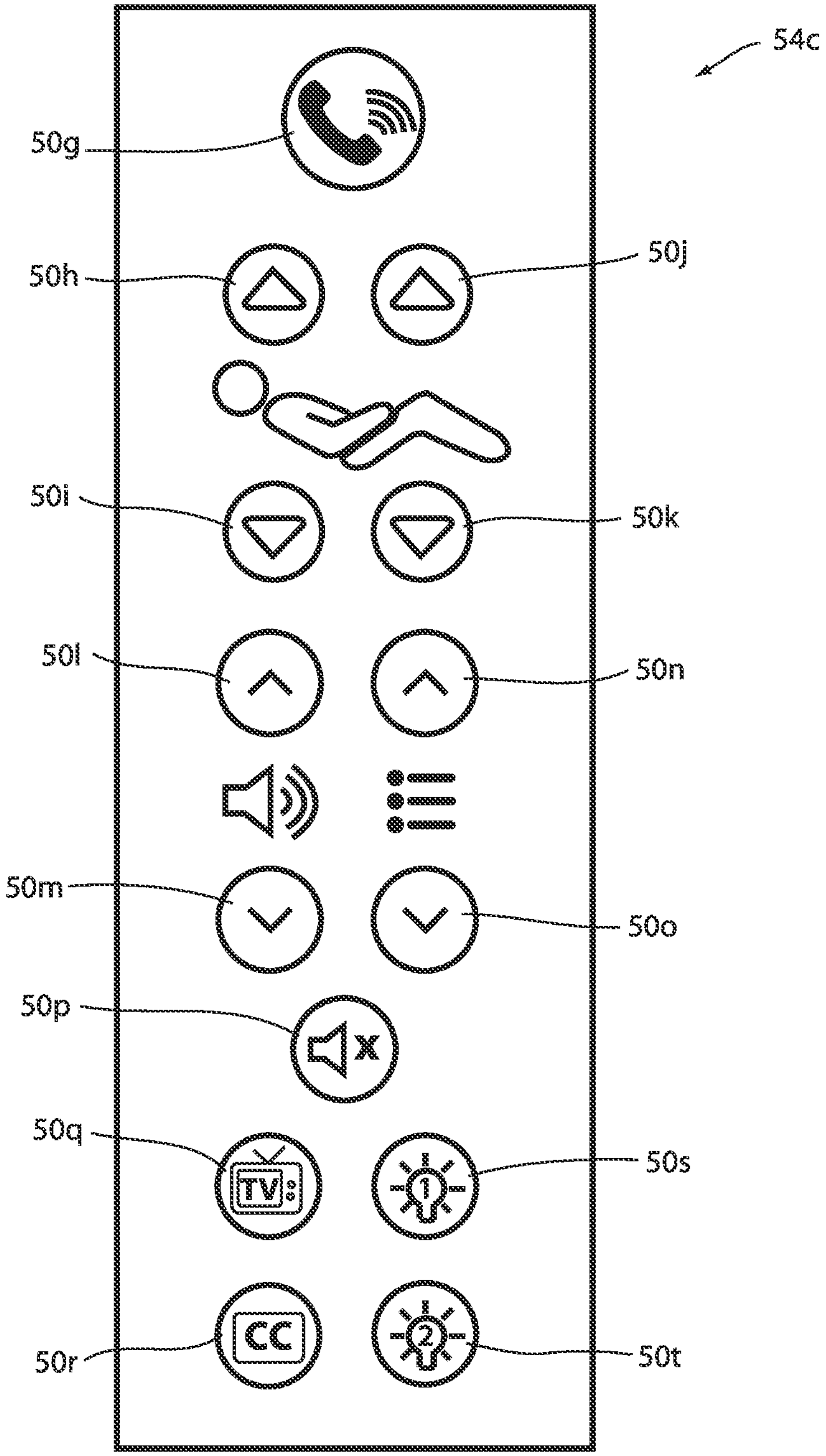
FIG. 3 is a plan view of an illustrative patient control panel of the patient support apparatus of FIG. 1.

FIG. 3 illustrates one example of a patient control panel 54*c* that may be incorporated into patient support apparatus 20 and positioned at a location on patient support apparatus 20 that is convenient for a patient to access while supported on support deck 30, such as on an interior side of one of the siderails 36. Control panel 54*c* includes a plurality of controls 50*g-t* that are intended to be operated by a patient. A nurse call control 50*g*, when pressed by the patient, sends a signal to a nurse call system requesting that a remotely positioned nurse talk to the patient. A Fowler-up control 50*h*, when pressed by the patient, causes a motorized actuator onboard patient support apparatus 20 to raise Fowler section 44 upwardly. A Fowler-down control 50*i*, when pressed by the patient, causes the motorized actuator to lower Fowler section 44 downwardly. A gatch-up control 50*j*, when pressed by the patient, causes another motorized actuator to raise a knee section of support deck 30, while a gatch-down control 50*k* causes the motorized actuator to lower the knee section of support deck 30.

A volume-up control 501, when pressed by the patient, causes patient support apparatus 20 to send a signal to an in-room television instructing it to increase its volume, while a volume down control 50*m*, when pressed, causes patient support apparatus 20 to send a signal to the television instructing it to decrease its volume. A channel-up control 50*n*, when pressed by the patient, causes patient support apparatus 20 to send a signal to the television instructing it to increase the channel number, while a channel-down control 50*o*, when pressed, causes patient support apparatus 20 to send a signal to the television instructing it to decrease the channel number.

A mute control 50*p*, when pressed, causes patient support apparatus 20 to send a signal to the television instructing it to either mute itself or unmute itself, depending upon whether the television is currently muted or unmuted. In other words, mute control 50*p* is a toggle control that alternatingly sends mute and unmute commands to the television when it is pressed.

Power control 50*q* is a toggle control that, when pressed, sends a signal to the television to either turn on or turn off, depending upon the television's current power status. Closed-captioning control 50*r* is another toggle control that, when pressed, sends a signal to the television to either turn on its closed-captioning feature or to turn off its closed captioning feature, depending upon whether the closed-captioning feature is currently on or off.

Control 50*s* is a toggle control that, when pressed, sends a signal to a first light to either turn on or turn off, depending upon the current state of that first light. Control 50*t* is another toggle control that, when pressed, sends a signal to a second light to either turn on or turn off, depending upon the current state of that second light. In some embodiments, the first light is a reading light and the second light is a room light, both of which are positioned off-board the patient support apparatus 20.

It will be understood that not only the number of controls 50 on control panel 54*c*, but also the functions of the controls 50 on control panel 54*c*, the layout of the controls 50 on control panel 54*c*, and/or other aspects of control panel 54*c* may be modified from what is shown in FIG. 3. In some embodiments, control panel 54*c* is implemented on a pendant controller that includes a cable that is plugged into a port on patient support apparatus 20. Still other manners of implementing control panel 54*c* are also possible.

Figure 4:
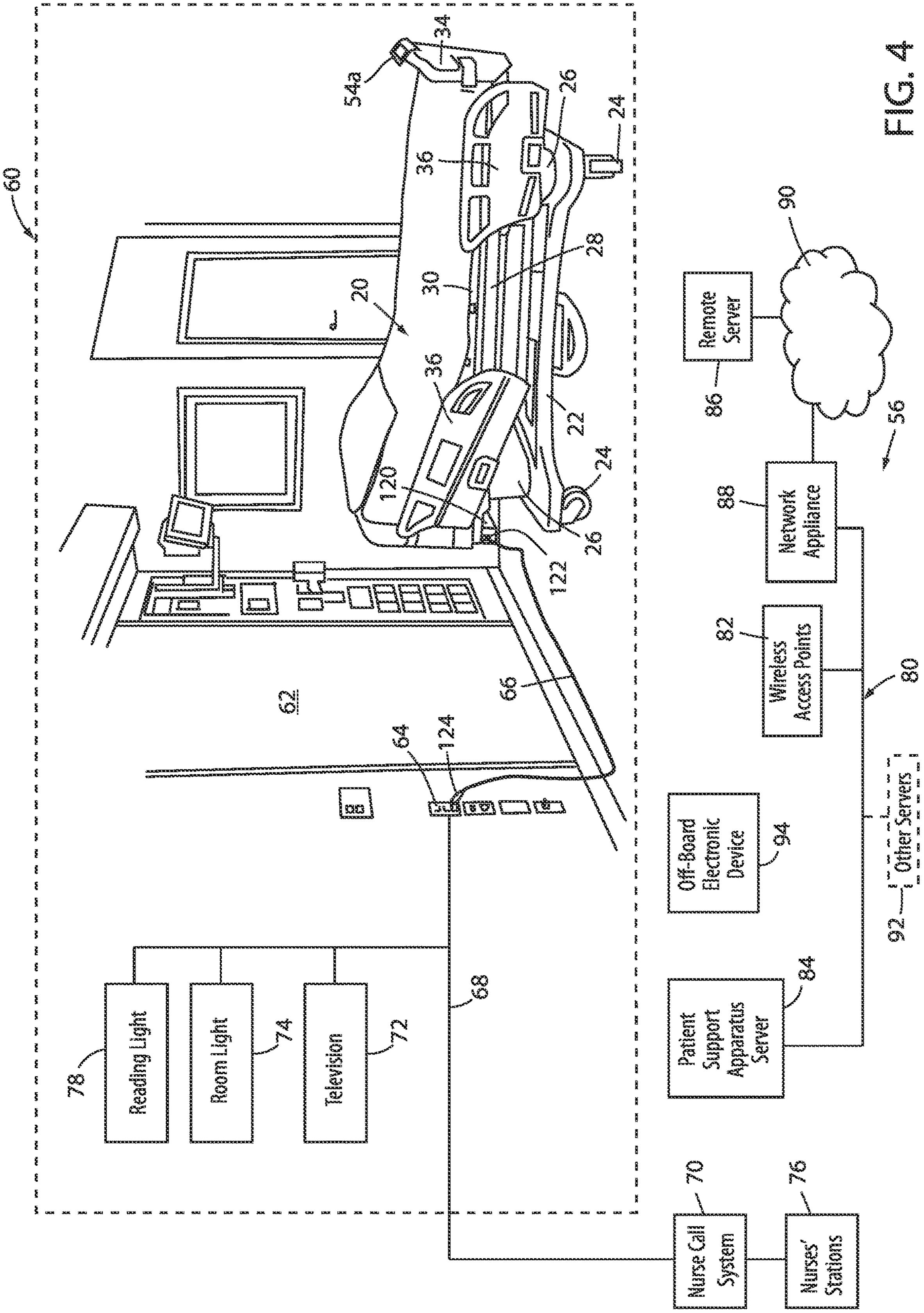
FIG. 4 is a diagram of the patient support apparatus of FIG. 1 shown coupled to the IT infrastructure of a healthcare facility in a first manner.

FIG. 4 illustrates patient support apparatus 20 positioned in a typical room 60 of a conventional healthcare facility 56. As shown therein, room 60 includes a headwall 62 into which a conventional communications outlet 64 is physically integrated. Communications outlet 64 is adapted to receive a nurse call cable 66 that physically connects at its other end to patient support apparatus 20. As will be discussed in greater detail below, nurse call cable 66 allows patient support apparatus 20 to communicate with a nurse call system, and one or more room devices positioned within room 60.

Communication outlet 64 is electrically coupled to one or more cables or other conductors 68 that electrically couple the communication outlet 64 to a nurse call system 70 and one or more room devices, such as a television 72, a room light 74, and/or a reading light 78. Conductors 68 are typically located behind headwall 62 and not visible. In some healthcare facilities, conductors 68 may first couple to a room interface circuit board that includes one or more conductors 68 for electrically coupling the room interface circuit board to room devices 72, 74, 78 and/or nurse call system 70. Still other communicative arrangements for coupling communication outlet 64 to nurse call system 70 and/or one or more room devices 72, 74, 78 are possible.

Room devices 72, 74, 78 are conventional room devices that are typically present in a conventional hospital room. In most cases, the particular brand and model of the television 72 and/or lights 74, 78 will vary from healthcare facility to healthcare facility, and may vary from room to room within the same healthcare facility. The different models and/or brands of televisions 72, room lights 74, and/or reading lights 78 are often controlled in different manners. For example, the signals that are input into a first brand of television in order to change a channel may require a first voltage level, while the signals that are input into a second brand of television in order to change the channel may require a second voltage level. Still further, apart from differences in voltage levels, the sequence of bits and/or other information that is sent to a television to change the channel, for example, may vary from brand to brand, or from model to model. Still other aspects of the control of the television 72 and/or lights 74, 78 may vary from brand to brand and/or from model to model. Thus, in order for a patient to properly control the television 72 and/or lights 74, 78 using one of the patient control panels 54*c*, patient support apparatus 20 and/or another device in communication with patient support apparatus 20 need to be properly configured to match the particular television 72 and/or lights 74, 78 that are positioned in the same room as the patient support apparatus 20. As will be discussed in greater detail below, this configuration data is stored, in at least one embodiment, in off-board headwall modules, and patient support apparatus 20 may be configured to both allow a user to use patient support apparatus 20 as a conduit for changing the configuration data stored in the off-board headwall module, and/or patient support apparatus 20 may be used as a conduit for allowing a remotely positioned person (e.g. a caregiver) to remotely control television 72, room light 74, and/or reading light 78 through patient support apparatus 20 and its associated off-board headwall module.

Returning to FIG. 4, nurse call cable 66 enables patient support apparatus 20 to communicate with nurse call system 70 and/or room devices 72, 74, 78. A patient supported on patient support apparatus 20 who activates a nurse call control (e.g. 50g; see FIG. 3) on patient support apparatus 20 causes a signal to be conveyed via nurse call cable 66 to the nurse call system 70, which forwards the signal to a one or more remotely located nurses (e.g. nurses at one or more nurses' stations 76). If the patient activates one or more room device controls (e.g. controls 501-*t;* see FIG. 3), one or more signals are conveyed via nurse call cable 66 to the room devices 72, 74, 78 that changes one or more features of these devices (e.g. the volume, channel, on/off state, etc.).

As is also shown in FIG. 4, patient support apparatus 20 is further configured to communicate with a local area network 80 of the healthcare facility 56. In the embodiment shown in FIG. 4, patient support apparatus 20 includes a wireless network transceiver 126 that communicates wirelessly with local area network 80. It will be understood, however, that in some embodiments, patient support apparatus 20 is adapted to communicate with network 80 via a wired connection, such as an Ethernet cable that plugs into an Ethernet port (e.g. an RJ-45 style port, an 8P8C port, etc.) built into patient support apparatus 20. In other embodiments, patient support apparatus 20 includes a wireless network transceiver, such as, but not limited to, a WiFi transceiver (e.g. IEEE 802.11) that wirelessly communicates with one or more wireless access points 82 of local area network 80. In still other embodiments, patient support apparatus 20 includes both a wired port for communicating with network 80 via a wired connection and a wireless connection for communicating with network 80.

Patient support apparatus 20 is configured to communicate with one or more servers on local area network 80 of healthcare facility 56. One such server is a patient support apparatus server 84. Patient support apparatus server 84 is adapted, in at least one embodiment, to receive status information from patient support apparatuses 20 positioned within healthcare facility 56 and distribute this status information to caregivers, other servers, and/or other software applications. In some embodiments, patient support apparatus server 84 is configured to communicate at least some of the status data received from patient support apparatuses 20 to a remote server 86 that is positioned geographically remotely from healthcare facility 56. Such communication may take place via a network appliance 88, such as, but not limited to, a router and/or a gateway, that is coupled to the Internet 90. The remote server 86, in turn, is also coupled to the Internet 90, and patient support apparatus server 84 is provided with the URL and/or other information necessary to communicate with remote server 86 via the Internet connection between network 80 and server 86.

It will be understood that the architecture and content of local area network 80 will vary from healthcare facility to healthcare facility, and that the example shown in FIG. 4 is merely one example of the type of network a healthcare facility may be employ. Typically, additional servers 92 will be hosted on network 80 and one or more of them may be adapted to communicate with patient support apparatus server 84. For example, an electronic health record server will typically be present in any healthcare facility, and in some cases may be in communication with patient support apparatus server 84 in order to receive patient data that is to be recorded in a patient's health record (e.g. weight readings taken from the scales built into patient support apparatuses 20; therapies provided to patients using a power mattress 42 onboard patient support apparatuses 20, etc.). Local area network 80 will also typically allow one or more electronic devices 94 to access the local area network 80 via wireless access points 82. Such electronic devices 94 include, but are not limited to, smart phones, tablet computers, portable laptops, desktop computers, and other types of electronic devices that include a WiFi capability and that are provided with the proper credentials (e.g. SSID, password, etc.) to access network 80.

In at least one embodiment, patient support apparatus server 84 is configured to communicate with one or more electronic devices 94 in order to allow such devices 94 to control one or more of the room devices 72, 74, 78 using one or more patient support apparatuses 20 as communication intermediaries. Thus, for example, if a user of an electronic device 94 wishes to turn off a television 72 positioned with a particular room, he or she can access patient support apparatus server 84 using electronic device 94 and its connection to local area network 80 via wireless access point 82. Patient support apparatus sever 84 executes an application that presents an authorized user of electronic device 94 with a set of menu options for controlling room devices 72, 74, 78 in at least one room 60, if not many or all, of the rooms 60 contained within healthcare facility 56. The user of electronic device 94 can then select the desired menu option on the screen of their electronic device 94 to turn on a room or reading light 74, 78 turn off a room or reading light 74, 78 turn on/off television 72, change the channel and/or volume of television 72, and/or change another aspect of television 72 (e.g. turn on/off closed captioning). The menu includes a selection of not only which rooms within healthcare facility 56 to control room devices 72, 74, 78 but also which bays within those rooms that include multiple bays (e.g. those rooms that are intended to house multiple patient support apparatuses 20) to control the corresponding room devices 72, 74, 78. The operation of this remote control of room devices via electronic device(s) 94 is described in more detail below with respect to FIG. 5.

Figure 5:
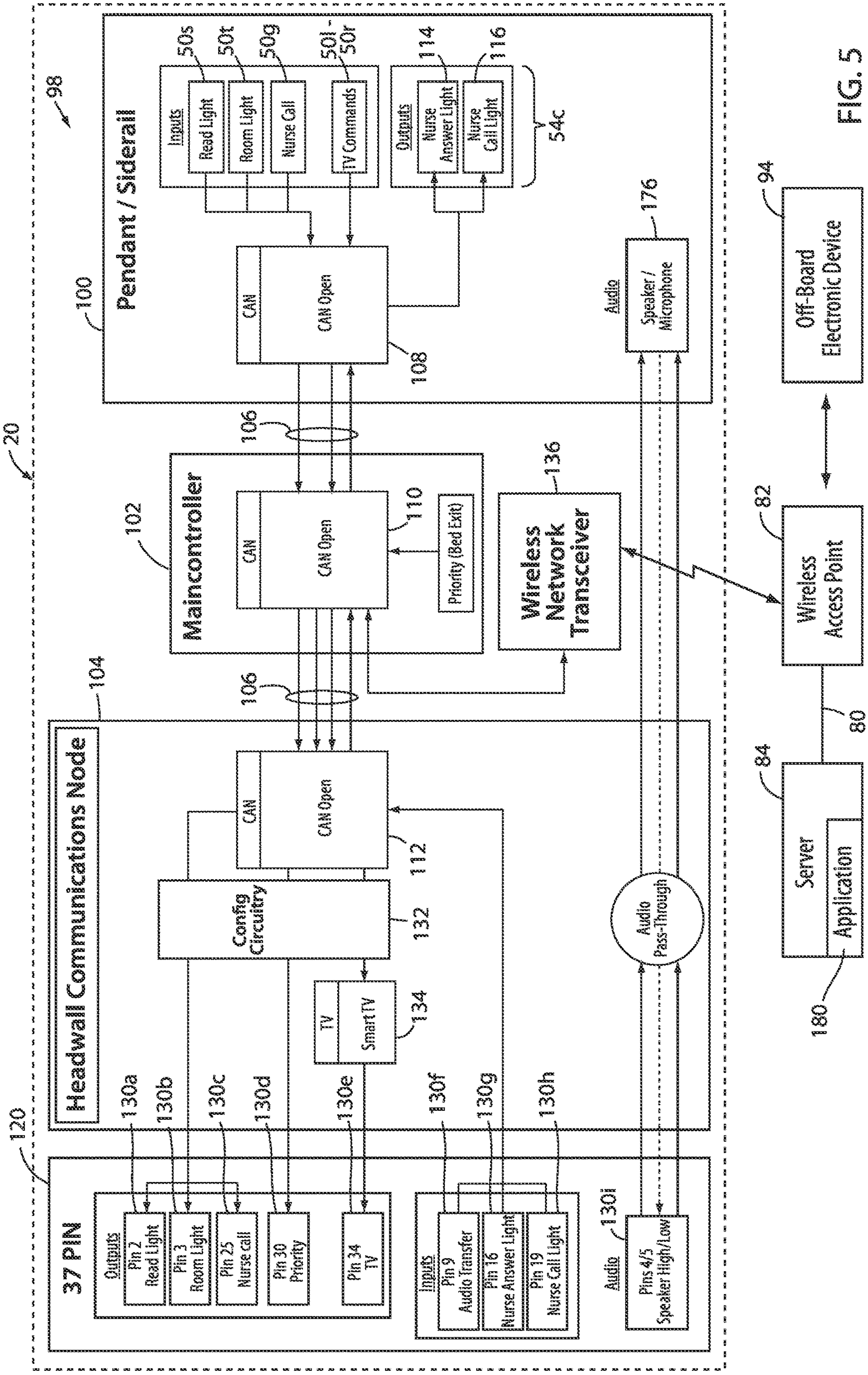
FIG. 5 is a diagram of the control system of the patient support apparatus of FIG. 1.

FIG. 5 depicts in more detail a control system 98 onboard patient support apparatus 20. Control system 98 includes a pendant/siderail node 100, a main node 102, and a headwall communication node 104. Each of nodes 100, 102, and 104 are part of an onboard embedded communications network 106. That is, each node 100-104 is communicatively coupled to each other via an onboard communication network 106, which, in the illustrated embodiment, is a Controller Area Network (CAN). It will be understood that other types of communication may be used in other embodiments (e.g. one or more of the following: an I-Squared-C bus, a Local Interconnect Network (LIN) bus, Firewire, RS-232, RS-485, a Universal Serial Bus (USB), Ethernet, and/or a Serial Peripheral Interface (SPI) bus, as well as non-bus communication). In still other embodiments, control system 98 may be implemented with fewer or greater numbers of nodes (including only a single node). Still other modifications are possible for control system 98, including, but not limited to, the elimination and/or replacement of onboard network 106.

Pendant/siderail node 100 includes pendant/siderail controller 108; main node 102 includes a main controller 110, and headwall communications node 104 includes a headwall communications controller 112. Each of controllers 108, 110, and 112 may take on a variety of different forms. In the illustrated embodiment, each of controllers 108, 110, and 112 is implemented as a conventional microcontroller. However, controllers 108, 110, and 112 may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 108, 110, and 112 when carrying out the functions described herein, as well as the data necessary for carrying out these functions, are stored in a corresponding memory (not shown) that is accessible to that particular controller 108, 110, and 112.

In some embodiments of patient support apparatus 20, siderail/pendant node 100 is physically positioned inside one or both of the head end siderails 36 of patient support apparatus 20 and includes patient control panel 54*c*. In other embodiments, pendant/siderail node 100 is physically positioned inside of a pendant that is coupled, typically via a cable, to patient support apparatus 20. In still other embodiments, patient support apparatus 20 may be configured with one or more pendant/siderail nodes 100 positioned inside of siderails 36 and also a pendant controller that is plugged into a pendant port on patient support apparatus 20 (and in communication with embedded network 106).

Control panel 54*c* of pendant/siderail node 100 includes a plurality of controls 50. Although FIG. 5 only illustrates controls 50*g* and 50*l* through 50*r*, it will be understood that pendant/siderail node 100 may include any or all of the controls 50 shown in FIG. 3. Pendant/siderail node 100 may also include additional controls 50 beyond what is shown in FIGS. 3 and/or 5, and/or it may include a selection of controls 50 that is different from the sets of controls 50 shown in FIGS. 3 and/or 5.

As shown in FIG. 5, pendant/siderail node 100 includes a nurse answer light 114 and a nurse call light 116. Pendant/siderail controller 108 is configured to light up nurse call light 116 when the user presses nurse call control 50*g* and receives an acknowledgement from the nurse call system 70 that a nurse call request has been successfully communicated to the nurse call system. Controller 108 is configured to light up nurse answer light 114 when a nurse actually responds to the nurse call placed by the user pressing on nurse call control 50*g*.

When a user presses on, or otherwise activates, any of controls 50 on control panel 54*c*, the pressing of those controls is detected by pendant/siderail controller 108. In response thereto, controller 108 sends a message on network 106 to headwall communication node 104 indicating which control(s) 50 were pressed. In some embodiments, the message is addressed (or otherwise identified) as being intended for headwall communication node 104 so that main node 102 does not need to act as a communications intermediary between node 100 and node 104. In other embodiments, controller 108 may send the message to node 104 via one or more intermediary nodes, such as main node 102. However the message travels to node 104, headwall communication controller 112 is programmed to receive the message and convey it in the appropriate manner to a headwall interface 120 incorporated into patient support apparatus 20.

Headwall interface 120 (FIG. 5) is an interface into which a conventional 37-pin nurse call cable, such as nurse call cable 66, is adapted to plug. That is, interface 120 is adapted to receive a 37-pin connector coupled to one end of a conventional nurse call cable 66. Nurse call cable 66 includes a first end having a first connector 122 (FIG. 4) and a second end having a second connector 124 (FIG. 4). First connector 122 is adapted to be plugged into headwall interface 120 positioned on patient support apparatus 20. Second connector 124 is adapted to be plugged into communication outlet 64. In many healthcare facilities 56, communication outlet 64 is configured as a 37-pin receptacle, although it will be understood that the principles of the present disclosure may be applied to communication outlets 64 and/or cables 66 having different numbers of pins.

Figure 16:
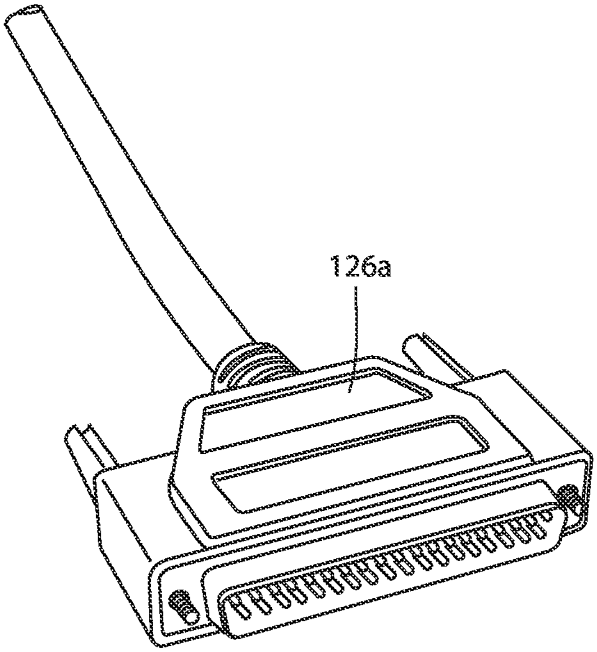
FIG. 16 (Prior Art)
FIG. 16 is a perspective view of a prior art 37-pin male cable connector.
Figure 17:
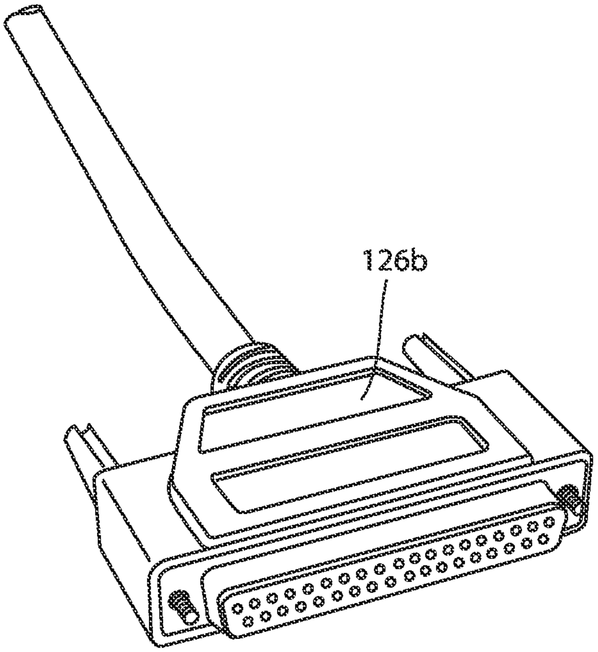
FIG. 17 (Prior Art)
FIG. 17 is a perspective view of a prior art 37-pin female cable connector.

One example of a male 37-pin connector 126a that may be used as first or second connector 122 or 124 is shown in FIG. 16. One example of a female 37-pin connector 126*b* that may be used as first or second connector 122 or 124 is shown in FIG. 17. Other types of 37-pin connectors may also be used, depending upon the configuration of communication outlet 64. Still further, in some healthcare environments, communication outlet 64 includes fewer pins and/or has an arrangement of pins that is shaped differently from what is shown in FIGS. 16 and 17. Patient support apparatus 20 may be adapted to communicate with all of these different types of communication outlets 64 via an appropriately selected cable (e.g. one with the proper connectors 122, 124 on its ends).

Headwall interface 120 (FIG. 5) includes a plurality of pins 130 that are adapted to electrically communicate with corresponding pins on nurse call cable 66. In some embodiments, pins 130 of headwall interface 120 may comprise female receptacles adapted to electrically couple to pins of cable 66 when cable 66 includes a male connector 122, or they may be pins 130 adapted to electrically couple to female receptacles when cable 66 includes a female connector 122. Pins 130 may alternatively be implemented as any type of metal, or electrically conductive, contact for establishing electrical communication between patient support apparatus 20 and nurse call cable 66.

Each pin 130 of headwall interface is adapted to convey certain information from patient support apparatus 20 to nurse call system 70 and/or room devices 72, 74, or vice versa. FIG. 18 shows one illustrative pin assignment for a conventional 37-pin connector. As can be seen in FIG. 18, each pin conveys different information. For example, pin 3 is used to convey information to room light 74 indicating that the occupant of patient support apparatus 20 has pressed a control (e.g. 50*t*) on patient support apparatus 20 to turn on or turn off the room light 74 in the particular room in which patient support apparatus 20 is located. In many instances, pin 3 is electrically tied to pin 27 and patient support apparatus 20 sends commands to room light 74 to turn on or turn off based on whether the electrical connection between pins 3 and 27 is open or closed. For some room lights 74, an open circuit between pins 3 and 27 indicates that the room lights should be turned off and a closed circuit between pins 3 and 27 indicates that the room light 74 should be turned on. For other room controls, the opposite may be true. That is, for some other room lights 74, an open circuit between pins 3 and 27 indicates the room light 74 should be turned on and a closed circuit between pins 3 and 27 indicates the room light 74 should be turned off.

As another example, pin 2 (FIG. 18) is commonly used to control a reading light 78. When the occupant of patient support apparatus 20 presses a control (e.g. 50*s*) on control panel 54*c* of patient support apparatus 20, controller 108 sends a message to headwall communications controller 112, and controller 112 reacts to the message by changing a voltage and/or by changing an open or closed state of an electrical circuit between pins 2 and 27 of headwall interface 120. For some reading lights 78, an open circuit between pins 2 and 27 indicates that the reading light 78 should be turned off and a closed circuit between pins 2 and 27 indicates that the reading light 78 should be turned on. For other reading lights 78, the opposite may be true.

When an occupant of patient support apparatus 20 presses on any of television controls 501-*r* on control panel 54*c,* pendant/siderail controller 100 sends a corresponding message over communication network 106 to headwall communications node 104 (FIG. 5). In response to receiving this message, headwall communication controller 112 outputs a corresponding signal on pins 33 and 34 of headwall interface 120. Because these pins are electrically coupled to the television 72 within room 60 via nurse call cable 66, communications outlet 64, and conductors 68, the television reacts appropriately in response to the commands entered by the occupant using controls 501-*r*.

In order for headwall communications controller 112 to determine how to properly respond to the messages it receives from pendant/siderail controller 108 in response to a user pressing on one or more of the controls 50 used to control television 72, room light 74, and/or reading light 78, controller 112 utilizes configuration circuitry 132 (FIG. 5). Configuration circuitry 132 is set up to maintain the pins 130 in their appropriate neutral state until a user presses on a corresponding control 50, as well as to apply the proper voltage to each of pins 130 in response to the user pressing the corresponding control 50. In some embodiments, configuration circuitry 132 includes one or more dip switches, or other devices, that are configurable to match the room device 72, 74, 78, and nurse call system 70 of the healthcare facility 56 in which the patient support apparatus 20 is installed. In other embodiments, configuration circuitry 132 may include onboard non-volatile memory that stores the necessary configuration data, along with appropriate circuitry to utilize this stored data to implement the necessary state changes in pins 130. In at least one embodiment, configuration circuitry 132 is implemented in any of the manners disclosed in commonly assigned U.S. patent publication 2018/0293849 published on Oct. 11, 2018, entitled PATIENT SUPPORT APPARATUSES WITH RECONFIGURABLE COMMUNICATION, the complete disclosure of which is incorporated herein by reference. Still other manners of implementing configuration circuitry 132 may also or alternatively be implemented according to the present disclosure.

Configuration circuitry 132 may, in some embodiments, include smart television control circuitry 134 (FIG. 5) that stores the sequence of signals that are to be sent for each brand (or a plurality of brands) of televisions that are necessary to control that television's channel, volume, mute, closed captioning, power state, HDMI input, etc. In such cases, either headwall communications controller 112 and/or configuration circuitry 132 informs smart TV control circuit 134 which brand of television (and, in some cases, which model) is in room 60, and smart TV control circuit 134 thereafter determines the correct signals to send in response to commands received from headwall communications controller 112 (which, in turn, receives the commands from control panel 54*c,* or as discussed in greater detail below, from off-board electronic device 94). The knowledge of which brand of television 72 is present in the room is conveyed to configuration circuitry and/or headwall communications controller 112 either by setting one or more dipswitches that are part of configuration circuitry 132, or by entering this information via one of the control panels (e.g. control panel 54*a*). In the latter case, the control panel 54 forwards the television brand information to headwall communications controller 112 over network 106.

In addition to room devices 72, 74, 78, the various pins 130 of headwall interface 120 also communicate information to nurse call system 70. This information is likewise often communicated by opening or closing the electrical connection between two pins. For example, when a patient presses a nurse call control, such as nurse call control 50*g* (FIG. 3), the electrical connection between pins 19 and 28 is typically changed by headwall communications controller 112 and configuration circuitry 132. These pins indicate to the nurse call system 70 that a nurse call request has been initiated by the occupant of patient support apparatus 20. Depending upon the particular nurse call system 70, it responds by illuminating one or more lights (e.g. a light in the hallway of the healthcare facility and/or a light at one or more of the nurses' stations 76). For some nurse call systems, the neutral state of the electrical connection between pins 19 and 28 should be open, while in other nurse call systems, the neutral state should be closed. Accordingly, configuration circuitry 132 is configured to properly match the particular nurse call system 70 with which it is going to communicate.

The term "neutral state" used herein refers to the state of the electrical connection between two pins 130 when no condition has been detected, or no desired action has been requested by the patient, caregiver, or patient support apparatus 20 itself. Thus, for example, for the pin that communicates a nurse call signal to the nurse call system (e.g. pin 30), the neutral state of that pin refers to its state when no nurse call control (e.g. 50*g*) has been pressed. In some nurse call systems, this neutral state will be closed with respect to a ground pin (e.g. common pin 31), while for other nurse call systems, this neutral state may be open with respect to the ground (e.g. common pin 31). As another example, for the pin that communicates a change to room light 74, the neutral state of pin 3 may refer to the electrical state of pin 3 relative to pin 27 (e.g. open or closed) when no change in room light 72 is being requested by a user (e.g. the patient has not pressed, or otherwise activated, control 50t).

Control system 98 also includes a wireless network transceiver 136 adapted to wirelessly communicate with one or more of the wireless access points 82 of the local area network 80 of the healthcare facility 56. As was noted, in some embodiments, transceiver 136 may be a conventional WiFi transceiver, although other types of wireless transceivers may be used. As was also noted previously, patient support apparatus 20 may also, or alternatively, include a wired transceiver (not shown) for communicating with network 80 via a wired connection.

Main controller 110 is adapted to receive commands from wireless network transceiver 136 that are intended to control one or more of room devices 72, 74, and/or 78. In response to those commands, main controller 110 executes the same or similar actions as does pendant/siderail controller 108 when it receives commands from controls 50. That is, main controller 110 forwards one or messages addressed to headwall communications controller 112 instructing it to control the corresponding pin(s) 130 in a manner corresponding to the received message. Thus, for example, if a remote user sends a command to turn on room light 74 to patient support apparatus, wireless network transceiver 136 forwards the command to main controller 110 which, in turn forwards it to headwall communication controller 112. Headwall communication controller 112, in turn, instructs configuration circuitry 132 to change the voltage and/or state of pin 3 such that the room light 74, which is in electrical communication with pin 3, turns on. In this manner, patient support apparatus 20 acts as a communication conduit to allow a remotely positioned person to remotely control any of room devices 72, 74, and/or 78.

In at least one embodiment, in order for a remotely positioned person to send a command to control any of room devices 72, 74, and/or 76 to patient support apparatus 20, the remotely positioned person must first log into a remote control application 140 that is executed by patient support apparatus server 84. The remotely positioned user is able to log into this remote control application 140 by using any off-board electronic device 94 that is able to access local area network 80 and server 84 (and that provides the necessary logon credentials to remote control application 140). Once logged on, remote control application 140 provides one or more screens that are displayed on the user's associated electronic device 94 that include controls for controlling room devices 72, 74, and/or 78. These remote controls, in some cases, are graphic icons that looks the same as, or similar to, the way controls 50 of control panel 54c look, thereby providing the remote user with the same visual image that a local user of control panel 54c would see. These remote controls may be the same set of controls 50 that are present on control panel 54*c,* a subset of those controls 50, a mix of some of the same controls and some different controls, or still other variations.

The remote controls that are presented to an authorized user of remote control application 140 may be visual controls displayed on a screen of electronic device 94 that must be touched by the user to remotely control room devices 72, 74, or 78 (if electronic device 94) includes a touch screen, or they may be visual controls that are displayed on a screen of electronic device 94 that are activated in a different manner (e.g. by selecting the control with a mouse and then mouse-clicking on the selected control, by pressing one or more keys on a keyboard or keypad, etc.). However presented, the activation of a selected control by the user of electronic device 94 causes electronic device 94 to send a signal to server 84 and remote application 140. If off-board electronic device 94 is wirelessly coupled to network 80, this is signal is sent by electronic device 94 to wireless access point 82, which then forwards it to server 84 and application 140 over network 80. If off-board electronic device 94 is coupled to network 80 via a wired connection, this signal is routed to server 84 and application 140 directly over network 80.

In response to receiving this remote control signal from electronic device 94, application 140 sends a corresponding command to patient support apparatus 20 via network 80, wireless access point 82 (in the example shown in FIG. 5) and network transceiver 136. As noted above, wireless network transceiver 136 forwards this command to controller 110, which in turn forwards it to headwall communication controller 112. Headwall communication controller 112 then instructs configuration circuitry 132 (and/or smart television control circuitry 134) to change the electrical state of, and/or place the necessary signals on, the corresponding pins 130 that will carry out the command received from remote control application 140. These state changes and/or signals are conveyed from the pins of headwall interface 120 to the pins of nurse call cable 66, which in turn transfers the state changes and/or signals to headwall communication outlet 64. Headwall communication outlet 64 then forwards these state changes and/or signals to the room device(s) 72, 74, and/or 78 via conductors 68.

For example, if a user of remote application 140 activates a remote control to increase the channel on television 72 in, say, room 402 of healthcare facility 56, the electronic device 94 that the user is using sends a signal to remote application 140 informing application 140 that the user has requested that television 72 in room 402 increase its channel. In response, application 140 sends a message to the patient support apparatus 20 in room 402 instructing it to increase the channel of the television 72 in that room. This is communicated to that patient support apparatus 20 via network transceiver 136, which in turn forwards it to main controller 110. Main controller 110 then forwards it to headwall communications controller 112. Headwall communications controller 112 instructs configuration circuitry 132 and/or smart television control circuitry 134 to output the correct voltage signals on pin 34 that will cause the particular brand of television in room 402 to increase its channel. Those voltage signals are conveyed via pin 34 to nurse call cable 66 which, in turn, conveys them to television 72 via communications outlet 64 and conductors 68. Television 72 then increases its channel.

In some embodiments, remote application 140 is incorporated into a larger software application that performs additional functions beyond merely allowing a user to remotely control room devices 72, 74, and/or 78. For example, in some embodiments, remote application 140 is incorporated into a caregiver assistance application that operates on server 84 and that receives status updates from patient support apparatuses 20 and/or that assists the caregiver in performing one or more other tasks, such as performing rounding duties, managing a patient's bed sore risk, managing a patient's fall risk, and/or other activities. One example of such a caregiver assistance application into which the functions of remote control application 140 may be incorporated is the caregiver assistance application 124 disclosed in commonly assigned U.S. patent application serial number 62/868,947 filed Jun. 30, 2019, by inventors Thomas Durlach et al. and entitled CAREGIVER ASSISTANCE SYSTEM, the complete disclosure of which is incorporated herein by reference.

Another type of software application that remote control application 140 may be incorporated into is a diagnostic and/or service application that is wholly or partially executed by server 84 and that is used to manage the servicing of, and/or perform diagnostic checks on, patient support apparatuses 20. One example of such a diagnostic and/or service application that remote control application 140 may be incorporated into is the equipment management service (e.g. local management server 34) disclosed in commonly assigned PCT patent application serial number PCT/US2017/041681 filed Jul. 12, 2017, by inventors David Becker et al. and entitled EQUIPMENT MANAGEMENT SYSTEM, the complete disclosure of which is incorporated herein by reference.

In alternative embodiments, it will be understood that, instead of, or in addition to, remote control application 140 executed on server 84, one or more of electronic devices 94 may be configured to include their own software application that communicates commands to patient support apparatus 20 for controlling room devices 72, 74, and/or 78. In such embodiments, electronic device 94 may communicate directly with patient support apparatuses 20 (e.g. bypass server 84), and/or they may communicate first with server 84 which then forwards their commands to patient support apparatuses 20.

In some embodiments, remote control application 140 is configured to allow a user to set up one or more schedules for one or more rooms 60 in order to control one or more of room devices 72, 74, and/or 78 according to one or more time-based and/or event-based schedules. Such schedules include, for example, the turning off of one or more room lights 74 at a certain time of day, the muting and activation of the closed captioning feature of television 72 at a certain time of day, the turning on of room light 74 at a certain time of day, the changing of a television channel to a specific channel in response to a specific event (e.g. a patient being newly assigned to a patient support apparatus 20), the turning off of room light 74, reading light 78, and/or television 72 when a patient has exited from patient support apparatus 20 for more than a predetermined time, and the turning on of room light 74, reading light 78, and/or television 72 when the patient returns to patient support apparatus 20 (and/or when the current time is within a user-designated window, such as evening hours). Still other examples are possible.

For those schedules that are based on time, patient support apparatus 20 may be configured to include an onboard clock that is used to determine when to implement the schedule. In some such embodiments, patient support apparatus 20 may utilize any of the clock functions disclosed in commonly assigned U.S. patent application Ser. No. 15/642,621 filed Jul. 6, 2017, by inventors Anuj Sidhu et al. and entitled PATIENT SUPPORT APPARATUSES WITH CLOCKS, the complete disclosures of which are incorporated herein by reference.

In those examples where the schedule is based partially or wholly on an event, the event may be determined, either wholly or partially, by one or more sensors onboard patient support apparatus 20 (e.g. an exit detection system and/or scale system), and/or by input from one or more other servers 92 on local area network 80 (e.g. an electronic health records server that informs patient support apparatus server 84 when a patient has had a medical treatment or therapy performed, an Admission, Discharge and Tracking (ADT) server that informs server 84 when a new patient has been assigned to a patient support apparatus 20, etc.). Still other devices that are in communication with patient support apparatus 20 (e.g. electronic device 94, patient support apparatus server 84, etc.) may also automatically trigger one or more changes to room devices 72, 74, and/or 78 based on one or more schedules that are input into patient support apparatus server 84.

In some embodiments, any schedule that a user sets up for one or more patient support apparatuses 20 is stored in patient support apparatus server 84 and patient support apparatus server 84 automatically sends corresponding commands to the patient support apparatuses 20 to change room devices 72, 74, and/or 78 at the appropriate time(s) (if the schedule is partially or wholly time-based), or in response to one or more detected events (if the schedule is partially or wholly event-based). In such embodiments, patient support apparatuses 20 need not include any data stored onboard regarding the schedule. In another embodiment, the schedule is forwarded to patient support apparatuses 20 and main controller 110 (or another controller, such as headwall communications controller 112) automatically makes the requisite changes to pins 130 in accordance with the schedule. In these latter embodiments, patient support apparatus server 84 need not retain any data concerning the schedule in its own memory after sending it to the appropriate patient support apparatuses 20. In still other embodiments, one or more schedules may be partially carried out by a controller onboard patient support apparatus 20 and partially carried out by patient support apparatus server 84.

In alternative embodiments of patient support apparatus 20, patient support apparatus 20 may be configured to wirelessly communicate with headwall communications outlet 64, instead of using a nurse call cable 66. One example of such a modified patient support apparatus 20*a* is shown and described below with respect to FIGS. 7, 8A and 8B. Unless otherwise stated herein, patient support apparatus 20*a* includes all of the same features and/or functionality as patient support apparatus 20, and may be modified in any of the same manners discussed herein with respect to patient support apparatus 20.

Figure 6:
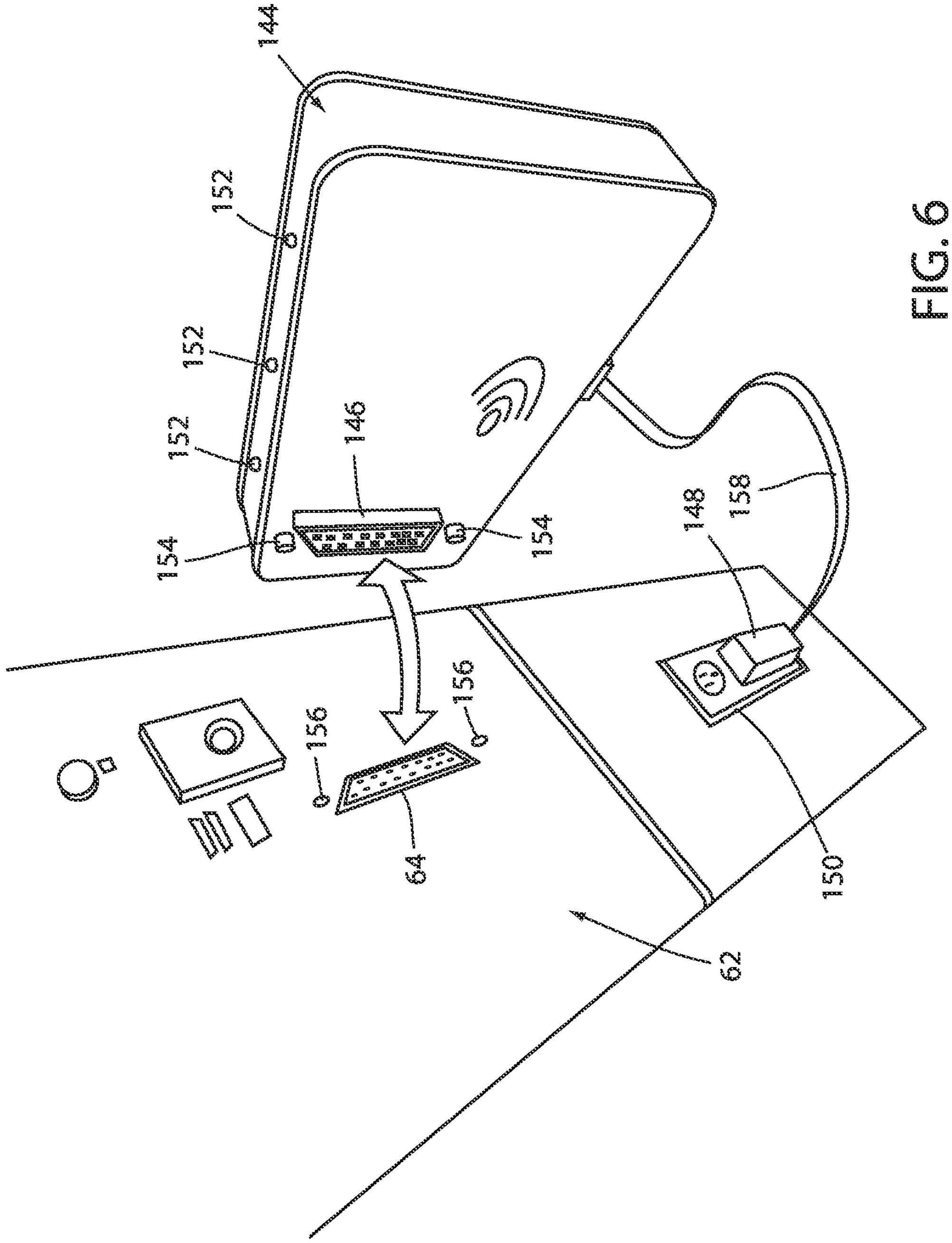
FIG. 6 is a perspective view of a first embodiment of a headwall module adapted to physically couple to an outlet in a headwall of a healthcare facility
Figure 7:
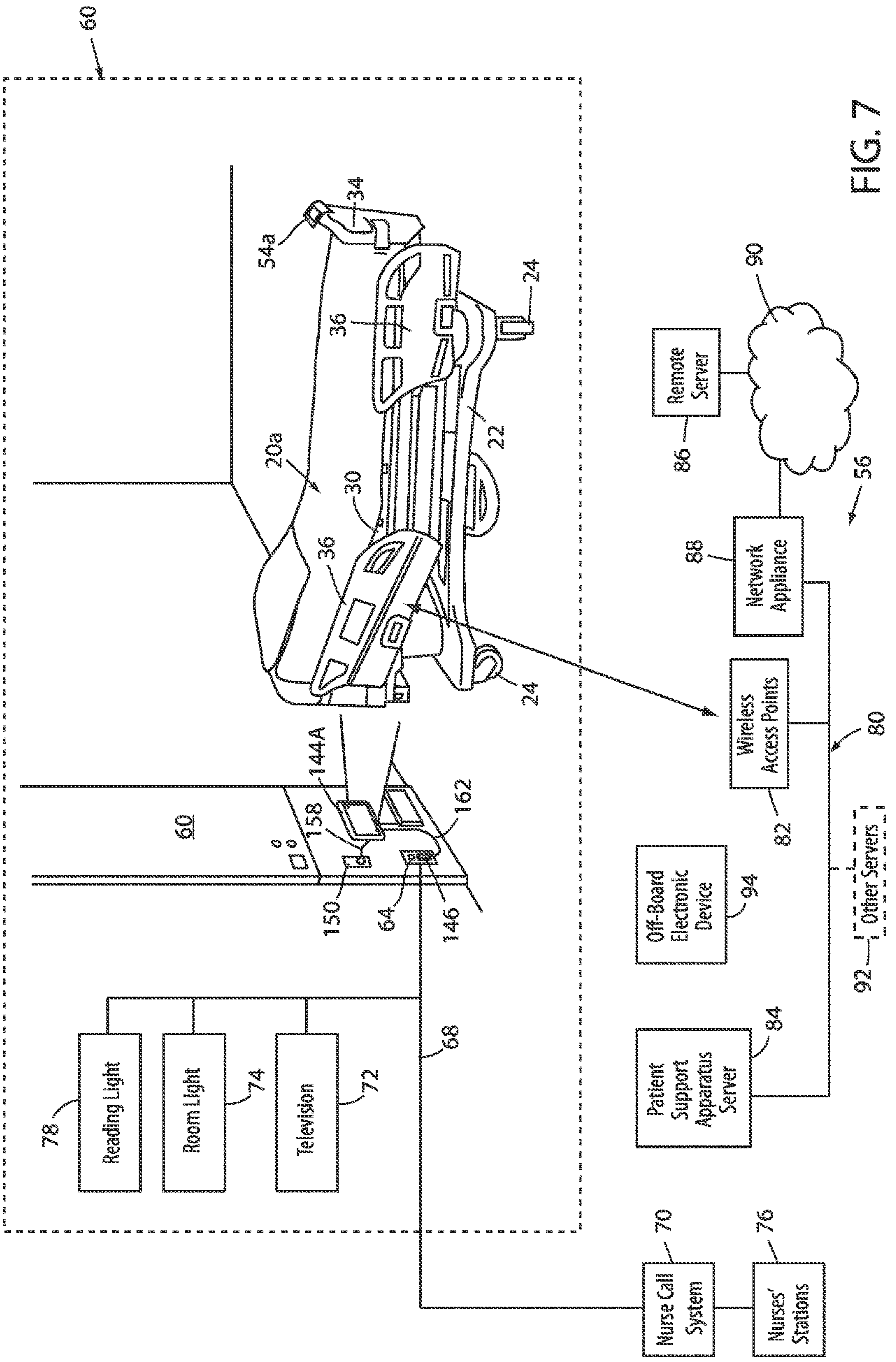
FIG. 7 is a diagram of an alternative patient support apparatus shown coupled to the IT infrastructure of a healthcare facility in a second manner.
Figure 8A:
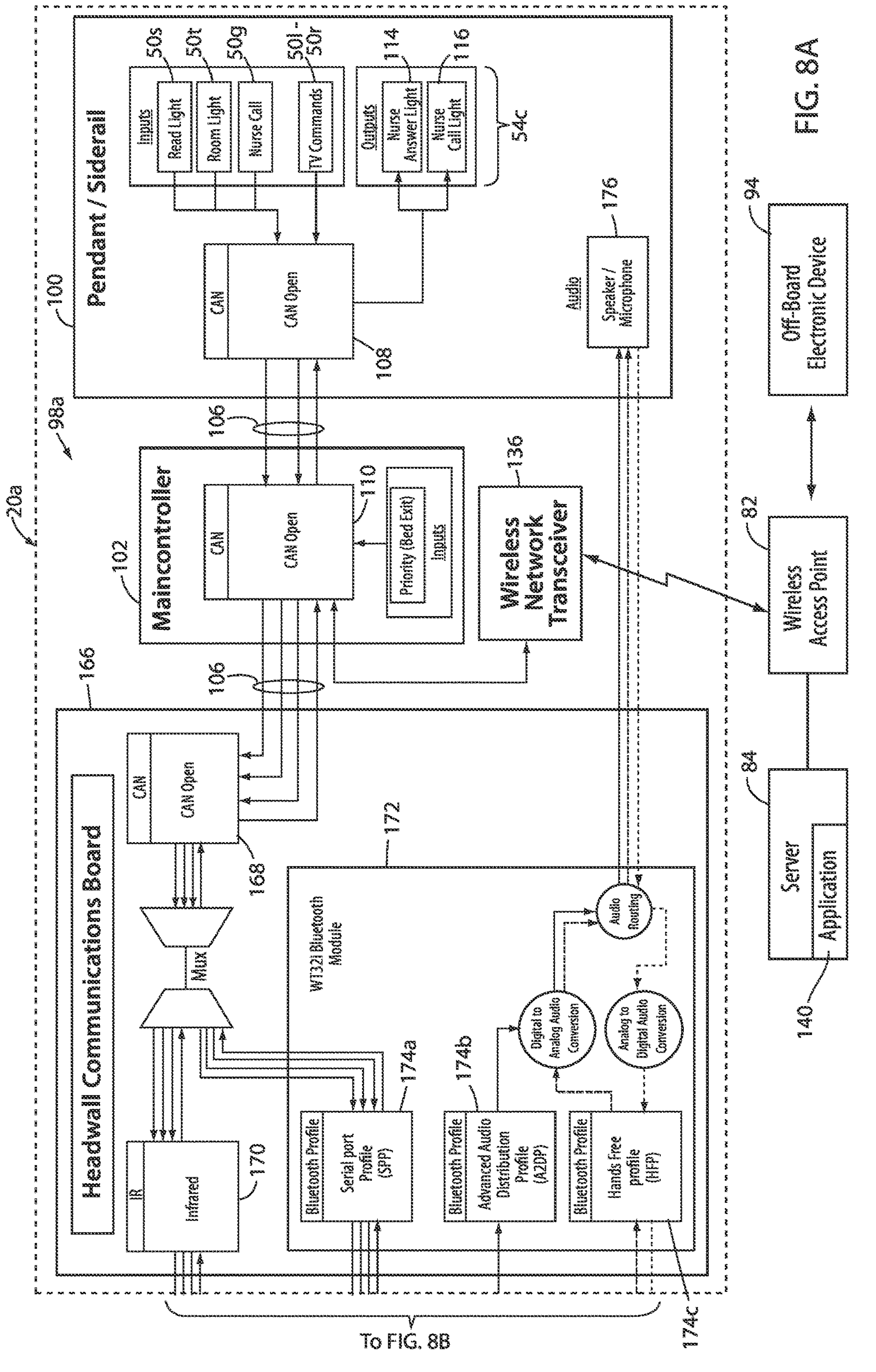
FIG. 8A is a first portion of a control system of the patient support apparatus of FIG. 7.
Figure 8B:
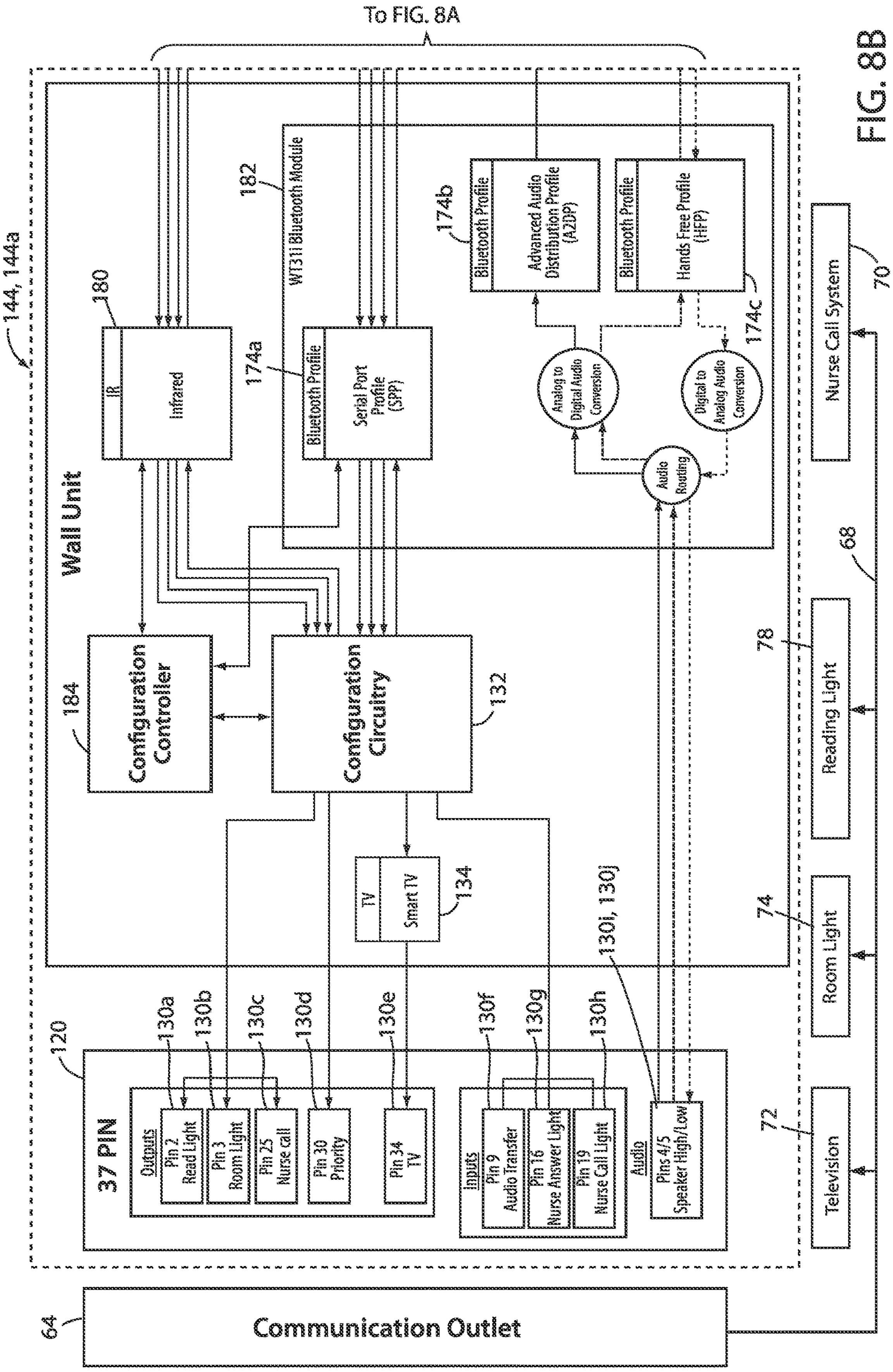
FIG. 8B is a second portion of the control system of the patient support apparatus of FIG. 7.

In order for patient support apparatus 20*a* to wirelessly communicate with headwall communications outlet 64, it utilizes a headwall module, such as a headwall module 144 (FIG. 6) or a headwall module 144*a* (FIGS. 7-8B). Headwall modules 144, 144*a* are adapted to wirelessly receive signals from patient support apparatus 20*a* and deliver the signals to communications outlet 64 in a manner that matches the way the signals would otherwise be delivered to communications outlet 64 if a conventional nurse call cable 66 were connected between patient support apparatus 20*a* and communications outlet 64. In other words, patient support apparatus 20*a* and headwall module 144, 144*a* cooperate to provide signals to communications outlet 64 in a manner that is transparent to communications outlet 64 such that outlet 64 cannot detect whether it is in communication with patient support apparatus 20 via a wired connection or it is in communication with patient support apparatus 20a via a wireless communication. In this manner, a healthcare facility can utilize the wireless communication abilities of one or more patient support apparatuses 20*a* without having to make any changes to their existing communication outlets 64.

In addition to sending signals received from patient support apparatus 20*a* to communications outlet 64, headwall modules 144, 144*a* (FIGS. 6-8B) are also adapted to forward signals received from communications outlet 64 to patient support apparatus 20*a*. Headwall modules 144, 144*a* are therefore adapted to provide bidirectional communication between patient support apparatus 20*a* and communications outlet 64. Such communication includes, but is not limited to, communicating command signals from any of controls 50 and/or from any of electronic device 94 to corresponding room devices 72, 74, and/or 78. Such communication also includes communicating audio signals between a person supported on patient support apparatus 20*a* and a caregiver positioned remotely from patient support apparatus 20*a*. The audio signals received by headwall modules 144, 144*a* from a microphone on patient support apparatus 20*a* are forwarded to communications outlet 64, and the audio signals received from communications outlet 64 are forwarded to a speaker onboard patient support apparatus 20*a*.

Headwall modules 144, 144*a* communicate the data and signals it wirelessly receives from patient support apparatus 20*a* to communications outlet 64 by utilizing headwall interface 120 (FIG. 8A). Headwall interface 120 of headwall module 144, 144*a* is adapted to electrically couple to communications outlet 64 and operate in the same manner as headwall interface 120 of patient support apparatus 20. That is, headwall interface 120 of headwall module 144, 144*a* is adapted to change the voltages and/or states of a plurality of pins 130 that are electrically coupled to corresponding pins inside of communications outlet 64 when headwall modules 144, 144*a* are physically coupled to communications outlet 64.

Headwall module 144 (FIG. 5) includes a connector 146 that is adapted to be physically inserted into headwall communications outlet 64. Connector 146 is a 37 pin connector that includes 37 pins adapted to be inserted into 37 mating sockets of communications outlet 64. As was described above with respect to nurse call cable 66, such 37 pin connections are one of the most common types of connectors found on existing headwalls of medical facilities for making connections to the nurse call system 70 and room devices 72, 74, and 78. Connector 146 is therefore configured to mate with one of the most common type of communication outlets 64 used in medical facilities. Such 37 pin connectors, however, are not the only type of connectors, and it will be understood that headwall module 144 can utilize different types of connectors 146 that are adapted to electrically couple to different types of communication outlets 64. One example of such an alternative communications outlet 64 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 64 and corresponding connectors 146 may be utilized.

Headwall module 144 also includes an electrical plug 148 positioned at an end of an electrical cord 158. Plug 148 is adapted to be inserted into a conventional electrical outlet 150. Electrical plug 148 and cord 158 enable headwall module 144 to receive power from the mains electrical supply via outlet 150. It will be appreciated that, in some embodiments, headwall module 144 is battery operated and plug 148 may be omitted. In still other embodiments, headwall module 144 may be both battery operated and include plug 148 so that in the event of a power failure, battery power supplies power to headwall module 144, and/or in the event of a battery failure, electrical power is received through outlet 150.

The embodiment of headwall module 144 shown in FIG. 6 also includes a plurality of status lights 152. Status lights 152 provide visual indications about one or more aspects of headwall module 144. For example, in some embodiments, the illumination of one of status lights 152 indicates that headwall module 144 is in successful communication with nurse call system 70 and/or patient support apparatus 20*a*. The illumination of one or more additional status lights 152 may also or alternatively indicate that power is being supplied to headwall module 144 and/or the status of a battery included within headwall module 144.

Headwall module 144 also includes a set of connection plugs 154 that are sized, shaped, and positioned to be able to be inserted into corresponding receptacles 156 adjacent communication outlet 64. When plugs 154 are inserted into receptacles 156, the pins of connector 146 will be aligned with the pins of communications outlet 64. Further, plugs 154 and receptacles 156 are configured to help ensure that connector 146 remains frictionally retained within communications outlet 64 after connector 146 is inserted into outlet 64. Plugs 154 and receptacles 156, in some embodiments, may be replaced with mounting screws and screw holes, respectively, in some embodiments.

Headwall module 144*a* of FIG. 7 differs from headwall module 144 of FIG. 6 in that headwall module 144*a* includes a connector cable 162 that extends between the body of headwall module 144 and connector 146. In other words, instead of connector 146 being mounted directly to the body of the headwall module, as connector 146 is with headwall module 144, connector 146 of headwall module 144*a* is mounted at the end of connector cable 162. Connector cable 162 therefore allows headwall module 144*a* to be mounted to headwall 62 at a location that is offset from communications outlet 64.

Headwall modules 144 and 144*a*, as noted, control the wireless communication between patient support apparatus 20*a* and communications outlet 64. In addition to communicating the signals used to control room devices 72, 74, and/or 78, headwall module 144, 144*a* may also communicate the following information between patient support apparatus 20*a* and communications outlet 64: messages indicating the current status of one or more siderails 36 of patient support apparatus 20*a* (e.g. whether the side rails are up or down, or have changed position); messages indicating the current status of a brake on patient support apparatus 20*a;* messages indicating the current status of the height of support deck 30 relative to base 22 (e.g. such as whether support deck 30 is at its lowest height or not); messages indicating the current angle of head section 44; messages indicating the current status of an exit detection system (e.g. whether the exit detection system is armed or not); messages indicating the current charging status of one or more batteries on patient support apparatus 20*a;* messages indicating the current status of an alternating current (A/C) power cable on patient support apparatus 20*a* (e.g. whether it is plugged in or not); diagnostic information about patient support apparatus 20*a;* messages containing patient data gathered from one or more sensors on board patient support apparatus 20*a;* message containing patient data gathered from one or more medical devices that are separate from patient support apparatus 20*a* but which communicate such data to patient support apparatus 20*a;* and/or any other messages containing information about patient support apparatus 20, the patient supported thereon, and/or a caregiver associated with the patient.

In addition to communicating the aforementioned data between patient support apparatus 20*a* and communications outlet 64, headwall modules 144, 144*a* may also communicate location data to patient support apparatus 20*a* that enables patient support apparatus 20*a* and/or patient support apparatus server 84 to determine the location of patient support apparatus 20*a* within healthcare facility 56. Such location determination may be carried out in any of the manner disclosed in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

Headwall modules 144, 144*a* may also perform additional functions. In some embodiments, headwall modules 144, 144*a* may perform any of the functions performed by the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNCIATION SYSTEM, the complete disclosure of which is incorporated herein by reference. In some embodiments, headwall modules 144, 144*a* may also, or alternatively, perform any of the same functions performed by the headwall interfaces 72 disclosed in commonly assigned U.S. patent application Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosure of which is also incorporated herein by reference. In still other embodiments, headwall modules 144, 144*a* may also, or alternatively, perform any of the same functions performed by the headwall units 66 disclosed in commonly assigned U.S. patent application Ser. No. 16/217,203 filed Dec. 12, 2018, by inventor Alexander Bodurka et al. and entitled SMART HOSPITAL HEADWALL SYSTEM, the complete disclosure of which is incorporated herein by reference.

Patient support apparatus 20*a* is shown in FIG. 7 communicatively coupled to communications outlet 64 by way of headwall module 144*a*. Patient support apparatus 20*a* is also shown communicatively coupled to a wireless access point 82 of local area network 80. Patient support apparatus 20*a* operates in the same way as that described above with respect to patient support apparatus 20 with the sole exception of communicating wirelessly with communications outlet 64, instead of communicating with outlet 64 via nurse call cable 66. Thus, patient support apparatus 20*a* is able to send commands to room devices 72, 74, and/or 78 by sending a wireless signal to headwall module 144*a*, which in turn relays those commands to the appropriate room device 72, 74, and/or 78 via its electrical connection to outlet 64. Further, patient support apparatus 20*a* is able to receive commands for controlling room devices 72, 74, and/or 78 from an off-board electronic device 94 (either directly or via patient support apparatus server 84), and to forward those commands to the corresponding room device 72, 74, and/or 78 using headwall module 144*a*.

FIGS. 8A and 8B illustrate a control system 98*a* included within patient support apparatus 20*a*. Those components of control system 98*a* that are the same as, and operate in the same manner as, the components of control system 98 (FIG. 5) of patient support apparatus 20 are labeled herein with the same reference numbers as control system 98. Those components of control system 98*a* that are different from control system 98 have been provided with a new reference number.

Control system 98*a* (FIG. 8A) differs structurally from control system 98 in two primary ways: control system 98*a* does not include headwall interface 120, and control system 98*a* includes a headwall communications board 166 that is adapted to wirelessly communicate with headwall module 144, 144*a*. Pendant/siderail node 100, main node 102, and wireless network transceiver 136 operate in the same manner as they do in control system 98, and their will not be repeated herein.

Headwall communications board 166 (FIG. 8A) includes a headwall board controller 168 that may take on any of the same physical forms as any of controllers 108, 110, and/or 112, which were previously described. Headwall communications board 166 also includes an infrared transceiver 170 and a Bluetooth transceiver 172. Transceivers 170 and 172 are adapted to wirelessly communicate with headwall module 144, 144*a*, and headwall communications board 166 controls the operation of transceivers 170 and 172. In some embodiments, the signals that are sent from patient support apparatus 20 to headwall module 144, 144*a* are sent over both transceiver 170 and 172 in order to provide redundancy to these communications. In other embodiments, these signals are sent over only one of the transceivers 170, 172, while in still other embodiments, some data is sent via both transceivers 170, 172, while other data is only sent via one of these two transceivers 170, 172.

Headwall board controller 168 is adapted to forward commands received from any of controls 50 (whether incorporated into the physical control panel 54*c* or a virtual control panel displayed on the screen of electronic device 94) to headwall module 144, 144*a*. Thus, for example, if a user of electronic device 94 sends a command to shut off television 72 to patient support apparatus 20 via wireless access point 82, network transceiver 136 receives this command and forwards it to headwall board controller 168 (either directly, or via main node 102). Headwall board controller 168, in turn, sends a signal to headwall module 144, 144*a* indicating that the television 72 is to be turned off. As noted, the signal may be sent via transceiver 170 or transceiver 172, or via both. As will be discussed in greater detail below, headwall module 144, 144*a* receives this signal and then adjusts the electrical characteristic of pin 34 (e.g. applies a sequence of voltages) of its headwall interface 120 in such a way so as to cause television 72 to be turned off.

As shown in FIG. 8A, Bluetooth transceiver 172 of headwall communications board 166 may utilize a plurality of different Bluetooth profiles 174*a-c* when communicating with headwall module 144, 144*a*. These include a serial port profile 174*a*, an advanced audio distribution profile 174*b*, and a hand free profile 174*c*. In the illustrated embodiment, Bluetooth transceiver 172 uses the serial port profile for communicating the commands to room devices 72, 74, and 78. Bluetooth transceiver 172 uses the other profiles 174*b* and 174*c* for transmitting the voice signals between patient support apparatus 20 and communications outlet 64 that arise when the patient onboard patient support apparatus 20*a* is talking to a remotely positioned nurse via nurse call system 70. The patient's voice signals are detected onboard patient support apparatus 20*a* via a microphone 176 and sent to headwall module 144, 144*a* using transceiver 172. The nurse's voice signals are received from headwall module 144, 144*a* and forwarded to a speaker 176 onboard patient support apparatus 20*a*. In some embodiments, the speaker and microphone are the same device, such as shown by microphone/speaker 176 in FIG. 8A, while in other embodiments, the speaker and microphone may be separate devices. Further, in some embodiments, the management of Bluetooth transceiver 172 in communicating audio signals between headwall module 144, 144*a* and the speaker, microphone, and/or speaker/microphone is carried out in any of the manners disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

Headwall module 144, 144*a* (FIG. 8B) includes an infrared transceiver 180, a Bluetooth transceiver 182, a headwall module controller 184, configuration circuitry 132, and, in at least some embodiments, smart television control circuitry 134. Infrared transceiver 180 is adapted to communicate with infrared transceiver 170 of patient support apparatus 20*a* using infrared waves. Bluetooth transceiver 182 if adapted to communicate with Bluetooth transceiver 172 of patient support apparatus 20*a* using RF waves in accordance with the conventional Bluetooth standard (e.g. IEEE 802.14.1 and/or the standard maintained by the Bluetooth Special Interest Group (SIG) of Kirkland, Washington, USA. Headwall module controller 184 is adapted to control the operation of transceivers 180, 182, and configuration circuitry 132, and headwall module controller 184 may be implemented as one or more microcontrollers, and/or in any of the same manners as controllers 108, 110, and/or 112, as discussed previously. Configuration circuitry 132 may be the same as the configuration circuitry 132 of patient support apparatus 20, and headwall interface 120 may be the same as headwall interface 120 of patient support apparatus 20.

When headwall module 144, 144*a* receives a command to change a feature of one of the room devices 72, 74, and/or 78 from one, or both, of transceivers 180, 182, headwall module controller 184 interprets the command so as to control configuration circuitry 132 in a manner that leads to the correct electrical change on the correct pins 130 of headwall interface 120. For example, if headwall module 144, 144*a* receives a command from patient support apparatus 20 for turning off reading light 78, headwall module controller 184 controls configuration circuitry 132 such that the electrical state of pin 2 (a.k.a. pin 130*a*) is changed. As noted previously, this change in state may vary, depending upon the model and/or implementation of the reading light 78. In some embodiments, headwall interface 120 may open the connection between pin 2 and pin 27 to turn off reading light 78; in other embodiments, it may close this connection; while in still other embodiments, it may change the voltage on pin 2 and/or perform some other electrical change.

Similarly, headwall module controller 184 and configuration circuitry 132 are configured to change the electrical characteristic of pin 3 (a.k.a. pin 130*b*) when a command is received from patient support apparatus 20*a* to change a status of room light 74. Headwall module controller 184 and configuration circuitry 132 are also configured to change the electrical characteristic of pin 25 (a.k.a. pin 130*c*) when a patient onboard patient support apparatus 20*a* places a call to a remotely positioned nurse (e.g. presses no nurse call control 50*g*). Still further, headwall module controller 184 and configuration circuitry 132 are also configured to perform the following: (a) change the electrical characteristic of pin 30 (a.k.a. pin 130*d*) when an exit detection system onboard patient support apparatus 20*a* detects a patient exit; (b) change the electrical characteristic of pin 34 (a.k.a. pin 130) when a command is received from patient support apparatus 20*a* to change a feature of television 72; (c) change the electrical characteristic of pin 9 (a.k.a. pin 130*f*) when the patient is speaking and patient support apparatus 20*a* is attempting to send audio signals to the remote nurse via headwall module 144, 144*a;* (d) read the current electrical state of pin 16 (a.k.a. pin 130*g*) to determine when a remotely positioned nurse has answered a patient call and to then send a command to patient support apparatus 20*a* to illuminate nurse answer light 114; (e) read the current electrical state of pin 19 (a.k.a. pin 130*h*) to determine when a remotely positioned nurse has placed a call to the patient and to send a command to patient support apparatus 20*a* and to illuminate nurse call light 116; and (f) transfer audio signals between patient support apparatus 20*a* and nurse call system 70 using pins 4 and 5 (a.k.a. pins 130*i* and 130*j*).

Although patient support apparatus 20 has been described herein as communicating with communication outlet 64 via cable 66 and patient support apparatus 20*a* has been described herein as communicating with outlet 64 via wireless communication through headwall module 144, 144*a,* it will be understood by those skilled in the art that either or both of patient support apparatuses 20 or 20*a* can be modified to include the circuitry of both control systems 98 and 98*a* such that they are able to communicate with outlet 64 both via wire and wirelessly. Such embodiments allow patient support apparatuses to communicate with outlet 64 in rooms where no headwall module 144, 144*a* is present, as well as to communicate with outlet 64 in rooms where no cable 66 is present and/or it is otherwise desired to communicate without a cable 66.

In addition to being able to control room devices 72, 74, and/or 78 in response to the activation of controls 50 and/or in response to commands received from electronic devices 94, patient support apparatus 20*a,* in some embodiments, is also configured to modify configuration circuitry 132 in response to inputs from one or more of control panels 54, as well as from electronic devices 94. In such embodiments, a user can change the configuration circuitry to make the communications to and from patient support apparatus 20*a* compatible with the particular nurse call system 70 and/or room devices 72, 74, and/or 78 that are present in a particular room. These configuration changes are discussed in more detail below with respect to FIGS. 9-15.

FIGS. 9-15 depict screens that are displayable on any of the displays of patient support apparatuses 20, of patient support apparatuses 20*a,* and/or of electronic devices 94. These screens allow a user positioned at patient support apparatus 20, 20*a,* or a user positioned at electronic device 94, to change the configuration circuitry 132 of either patient support apparatuses 20, 20*a* or headwall modules 144, 144*a* so that the patient support apparatuses 20, 20*a* are able to properly communicate with the nurse call system 70 and the room devices 72, 74, and 78. The screens shown in FIGS. 9-15 are therefore displayed on display 52 of patient support apparatuses 20, 20*a* under the control of main controller 110 (or another controller responsible for overseeing the operation of display 52), or they are displayed on a screen of an electronic device 94 under the control of remote control application 140 (or otherwise interacting with remote control application 140).

Figure 9:
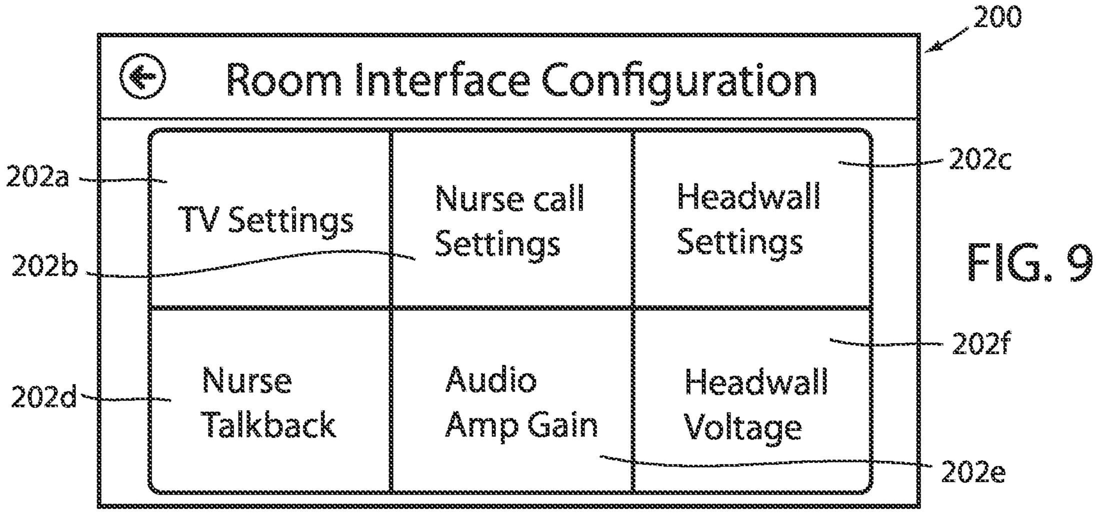
FIG. 9 is an illustrative master configuration control screen displayable on the display of any of the patient support apparatuses disclosed herein or a display of any of the off-board electronic devices disclosed herein.

FIG. 9 illustrates one example of a master configuration control screen 200 that, as noted, is displayable on display 52 of control panel 54*a* and/or on a display of any of electronic devices 94 that are executing, or in communication with, remote control application 140. Master configuration control screen 200 includes six configuration options 202*a-f* that, when selected, bring the user to the six screens shown in FIGS. 10-15, respectively. These six screens allow the user to change and control various configuration settings that are used by patient support apparatus 20, 20*a* when communicating with communications outlet 64, whether via cable 66 or wirelessly using headwall module 144, 144*a*. These six screens will be discussed in more detail below with respect to display 52 of patient support apparatus 20, 20*a,* but it will be understood that this discussion applies equally to the displays of electronic devices 94 that are executing, or in communication with, remote control application 140.

Figure 10:
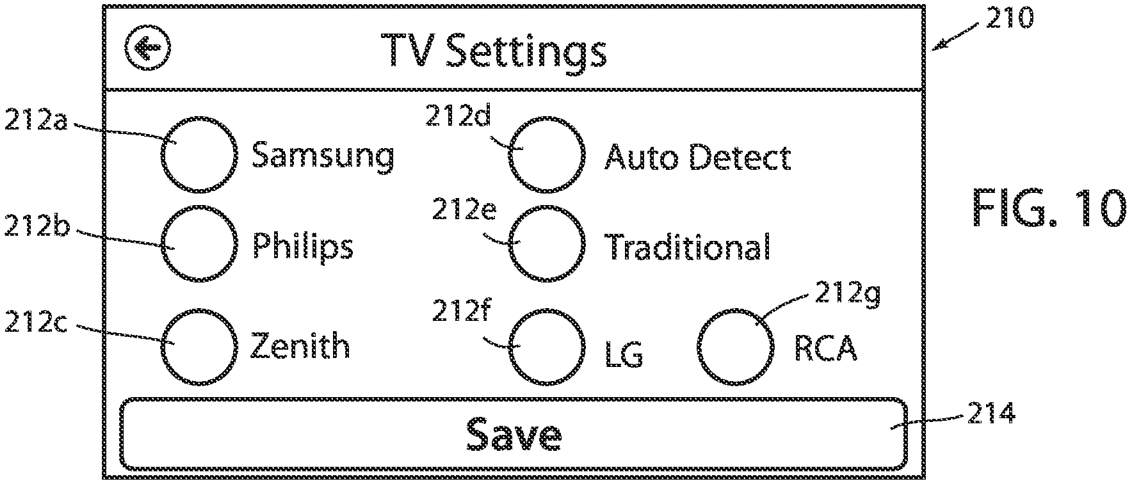
FIG. 10 is an illustrative TV settings control screen displayable on the display of any of the patient support apparatuses disclosed herein or a display of any of the off-board electronic devices disclosed herein.

If a user selects TV settings option 202*a* of master configuration control screen 200 (FIG. 9), display 52 of control panel 54*a* displays a TV settings control screen 210, such as shown in FIG. 10. TV settings control screen 210 includes a plurality of TV options 202*a-g*. Each option 202*a-g* corresponds to a different set of signals that are sent to television 72 when a user presses on controls 501-50r of control panel 54*c.* Most options correspond to a particular brand of TV because most TV manufacturers program all of their models of televisions to respond to the same set of signals for implementing the same changes. In other words, for example, all Samsung televisions 72 will typically increase their channel in response to a first sequence of signals, decrease their channel in response to a second sequence of signals, increase their volume in response to a third sequence of signals, and perform the other functions controlled by controls 50*l*-50*r* in response to still other sequences of signals, and the set of sequences for controlling all of these functions is the same for all Samsung brand televisions. However, other manufacturers of televisions may program their televisions to change channels, for example, in response to a different sequence of signals than what the Samsung televisions use. Accordingly, TV settings control screen 210 allows a user to select which brand of television is present in the room 60 in which patient support apparatus 20, 20*a* is located, and this information is then communicated to smart TV control circuitry 134. As noted smart TV control circuitry 134 stores in its memory all of the signal sequences that are used by all, or substantially all, television manufacturers and selects which set of sequences to use to control television 72 based on the users selection on screen 210.

In addition to listing a plurality of specific brands, TV settings control screen 210 (FIG. 10) also includes an auto-detect option 212*d*. If the user selects the auto-detection option 212*d*, headwall communication controller 112 (for patient support apparatuses 20) or headwall module controller 184 (for patient support apparatuses 20*a*) measures the voltage across pins 33 and 34 (see FIG. 18) of communications outlet 64 (which is electrically coupled to headwall interface 120). Controller 112 and/or 184 attempts to determine the television brand based on the measured voltage and the fact that different television brands output different voltages on their remote control lines. Based on the detected voltage, controller 112 and/or 184 makes a conclusion about the brand of television and implements the corresponding configurations settings for that brand. If controller 112 and/or 184 are unable to determine the brand based on the measured voltage, a message may be shown on display 52 indicating that the television brand could not be determined.

In an alternative embodiment, headwall communication controller 112 is adapted to automatically detect a television brand (or model) by automatically sending a series of test commands to the television 72 and analyzing its response (as measured through changes in the audio signals received from the television 72). From this information, controller 112 is able to determine what set of controls to use with television 72. The series of test commands include, but are not necessarily limited to, commands that change the audio output of television 72, such as commands to increase the volume, decrease the volume, mute the television 72, turn off the television 72 (in which case audio signals will cease completely), and turn on the television. By sending these test commands and determining which test commands lead to the expected behavior of the television's audio response, and which ones don't, headwall communications controller 112 (or headwall module controller 184) is typically able to determine the brand of television 72. When so determined, it informs smart television control circuit 134, which then uses the appropriate set of commands for controlling television 72. If controllers 112 and/or 184 are unable to determine the brand of television, a message may be shown on display 52 indicating that the television brand could not be determined. Other types of auto-detection algorithms may also or alternatively be used.

TV settings control screen 210 (FIG. 10) also includes a traditional option 212e. This option corresponds to older televisions that only respond to remote control signals by increasing the channel until the maximum channel is reached, then turning off, then turning on at the lowest channel, and then repeating this cycle. Such televisions are not able to follow commands to decrease their channel, turn on/off muting and/or closed captioning, or change their volume. In response to a user selecting traditional option 212*e*, headwall communications controller 112 (for patient support apparatuses 20) and headwall communications board 166 (for patient support apparatuses 20*a*) send the same signal to communications outlet 64 regardless of which television control 50*l*-50*r* the user activates because the television 72 is not able to be remotely controlled in any other manner than the aforementioned cycle, and this same signal prompts the television 72 through this cycle. In some embodiments, control panel 54*c* and/or another control panel displays a message to the patient when he or she attempts to control such a standard television 72. The message informs the patient that the standard television will only respond to the patient's activation of controls 50*l*-*r* by progressing through the aforementioned cycle, or otherwise informs the patient that controls 50*l*-50*r* are not defective, but instead are operating as intended for the standard television 72.

Figure 11:
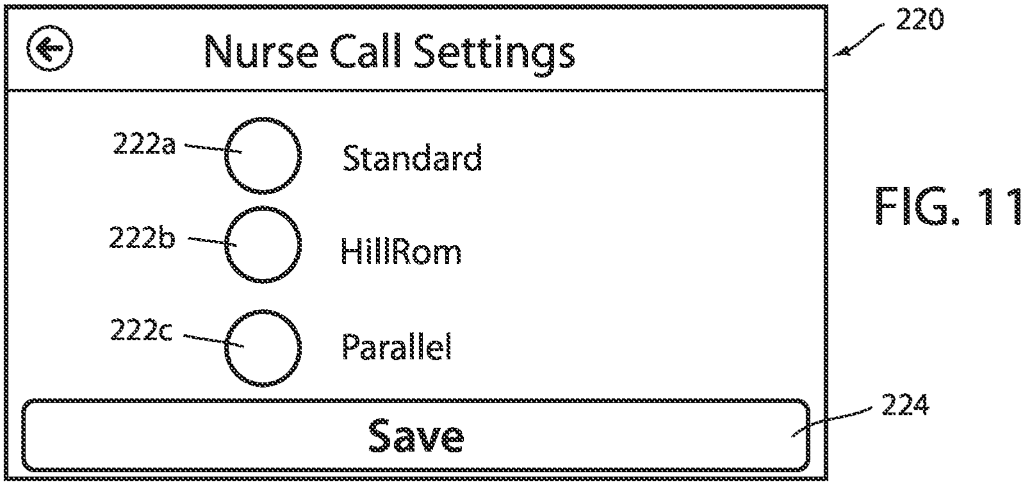
FIG. 11 is an illustrative nurse call settings screen displayable on the display of any of the patient support apparatuses disclosed herein or a display of any of the off-board electronic devices disclosed herein.

If a user selects nurse call settings option 202*b* of master configuration control screen 200 (FIG. 9), display 52 of control panel 54*a* displays a nurse call settings control screen 220, such as shown in FIG. 11. Nurse call settings control screen 220 includes a plurality of nurse call setting options 222*a-c*. Each of the options 222*a-c* corresponds to different manners in which nurse call systems communicate with patient support apparatus 20, 20*a*, and vice versa. More specifically, for a first type of nurse call system, a first set of pins are electrically shorted; for a second type of nurse call system, a second set of pins are electrically shorted; and for a third type of nurse call system, both the first and second sets of pins are electrically shorted. In the example shown in FIG. 11, these three types of nurse call systems are labeled as "standard," "Hill-Rom," and "parallel."

If the user selects the standard option 222*a* (FIG. 11), controller 112 (for patient support apparatuses 20) or controller 184 (for patient support apparatuses 20*a*) is adapted to change configuration circuitry 132 such that it will electrically short together pins 30 and 31 in response to an exit detection alert (as detected by an exit detection system onboard patient support apparatus 20, 20*a*) and it will electrically short together pins 25 and 26 in response to a nurse call placed by the patient on patient support apparatus 20, 20*a*.

If the user selects the Hill-Rom option 222*b* (FIG. 11), controller 112 (for patient support apparatuses 20) or controller 184 (for patient support apparatuses 20*a*) is adapted to change configuration circuitry 132 such that it will electrically short together pins 25 and 26, as well as pins 30 and 31, in response to an exit detection alert (as detected by the exit detection system onboard patient support apparatus 20, 20*a*). Additionally if the user selects the Hill-Rom option 222*b* (FIG. 11), controller 112 (for patient support apparatuses 20) or controller 184 (for patient support apparatuses 20*a*) is adapted to change configuration circuitry 132 such that it will electrically short together pins 25 and 26 in response to a nurse call placed by the patient on patient support apparatus 20, 20*a*.

If the user selects the parallel option 222*c* (FIG. 11), controller 112 (for patient support apparatuses 20) or controller 184 (for patient support apparatuses 20*a*) is adapted to change configuration circuitry 132 such that it will electrically short together pins 25 and 26, as well as pins 30 and 31, in response to an exit detection alert (as detected by the exit detection system onboard patient support apparatus 20, 20*a*). Additionally if the user selects the parallel option 222*c* (FIG. 11), controller 112 (for patient support apparatuses 20) or controller 184 (for patient support apparatuses 20*a*) is adapted to change configuration circuitry 132 such that it will perform the same electrical shorting in response to a nurse call placed by the patient on patient support apparatus 20, 20*a* (i.e. shorting together pin 25 with pin 26, and shorting together pin 30 with pin 31).

Figure 12:
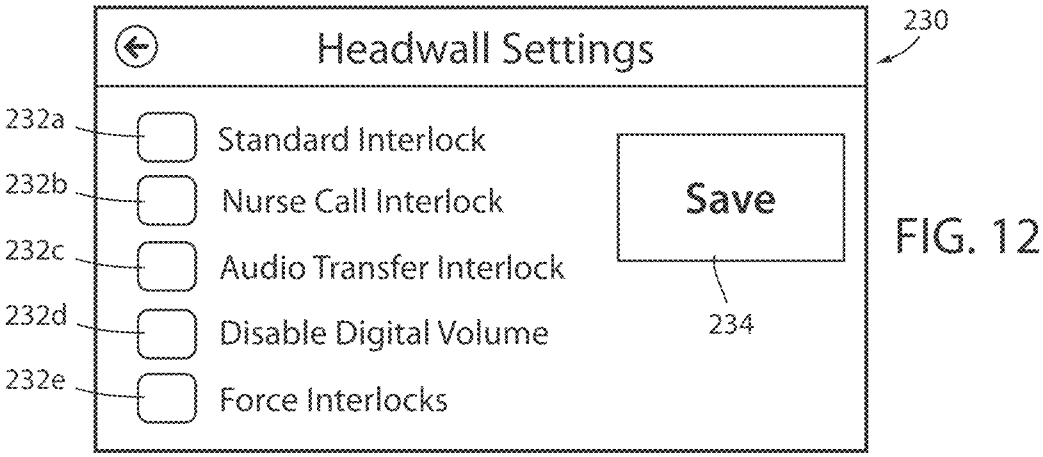
FIG. 12 is an illustrative headwall settings screen displayable on the display of any of the patient support apparatuses disclosed herein or a display of any of the off-board electronic devices disclosed herein.

If a user selects headwall settings option 202*c* of master configuration control screen 200 (FIG. 9), display 52 of control panel 54*a* displays a headwall settings control screen 230, such as shown in FIG. 12. Headwall settings control screen 230 includes a plurality of headwall setting options 232*a-e*. Generally speaking, four of these settings relate to how the nurse call system 70 determines that a patient support apparatus 20, 20*a* is currently connected or disconnected to communications outlet 64, and one of these settings relates to controlling the volume of television 72. More specifically, each of the options 232*a-c* and 232*e* corresponds to different manners in which patient support apparatus 20, 20*a* communicates to the nurse call system 70 that it is present and communicatively coupled to the nurse call system via communication outlet 64, and option 232*d* corresponds to how patient support apparatus 20, 20*a* changes the volume of the television audio signals that are output from speaker 176.

Options 232*a-c* and 232*e* specify different types of interlocks, which refers to which pins 130 are electrically shorted together by headwall interface 120 when headwall interface 120 is plugged into outlet 64. The coupling together of these pins is detected by the nurse call system 70, such as by sending a signal to one of the two pins that are coupled together and looking for the signal to return on the other one of the two pins 130 that are coupled together. If the return signal is detected, nurse call system 70 is able to confirm that patient support apparatus 20, 20*a* is communicatively coupled to itself. If the nurse call system 70 does not detect the return signal, it concludes patient support apparatus 20, 20*a* is not coupled to nurse call system 70 and issues what is known as a cord-out alert, which is an alert communicated to caregivers that the patient support apparatus 20, 20*a* in a particular room is no longer communicatively coupled to the nurse call system 70 (and the patient associated with that patient support apparatus is therefore unable to communicate with nurse call system 70). Because different nurse call systems 70 use different pairs of pins to detect the presence of a patient support apparatus, patient support apparatuses 20, 20*a* need to be properly configured to match the system used by a particular healthcare facility. Headwall settings control screen 230 allows the user to make this selection.

In at least one embodiment, controller 112 (for patient support apparatuses 20) or controller 184 (for patient support apparatuses 20*a*) is configured, by default, to not couple together any of the interlock pins until controller 112 (or 184) detects a voltage across an expected set of pins applied by the nurse call system 70, or the user manually selects a "force interlocks" option (discussed in more detail below). In this manner, the interlock configurations are not implemented until controller 112 (or 184) verifies that it is coupled to the communications outlet 64 and nurse call system 70. This default configuration setting helps to ensure that neither patient support apparatus 20 nor headwall module 144, 144*a* electrically short together any interlock pins prior to coupling to the nurse call system 70 and ensuring that the correct interlock pins are coupled together. This helps avoid damage that may otherwise occur for some nurse call systems 70 if the wrong interlock pins are coupled together.

If the user selects standard interlock option 232*a* (FIG. 12), controller 112 (for patient support apparatuses 20) or controller 184 (for patient support apparatuses 20*a*) is adapted to change configuration circuitry 132 such that pins 10 and 11 (FIG. 18) are electrically coupled together. In other words, headwall interface 120 is configured to implement an electrical jumper between pins 10 and 11 such that any signals sent to interface 120 from the nurse call system 70 on pin 10 are returned on pin 11, and vice versa.

If the user selects nurse call interlock option 232*b* (FIG. 12), controller 112 (for patient support apparatuses 20) or controller 184 (for patient support apparatuses 20*a*) is adapted to change configuration circuitry 132 such that pins 7 and 25 are electrically coupled together.

If the user selects audio transfer interlock option 232*c* (FIG. 12), controller 112 (for patient support apparatuses 20) or controller 184 (for patient support apparatuses 20*a*) is adapted to change configuration circuitry 132 such that pins 8 and 9 are electrically coupled together. I If the user selects any of the transfer interlock options 232*a-c,* configuration circuitry 132 is configured to only implement the electrical shorting of the aforementioned pins together in response to detecting one or more voltages between selected pins of the communications outlet 64. Such pins include, but are not limited to, pins 25 and 26, as well as pins 30 and 31. If controller 112 or controller 184 does not detect a voltage between either or both of these sets of pins (as sensed by configuration circuitry 132 and/or other sensors in headwall interface 120), it is configured, in some embodiments, to not implement any of the headwall setting options 232*a-c*. This is done for safety purposes as some nurse call systems can be damaged by shorting the pins of options 232*a-c* together.

In some nurse call systems, the voltages that the nurse call system 70 applies between pins 25 and 26 and/or between pins 30 and 31 are not sent applied by the nurse call system 70 until a patient support apparatus 20, 20*a* is coupled to communications outlet 64. In such systems, there is the possibility of a stalemate situation where patient support apparatus 20, 20*a* might not be shorting together any of the pins of options 232*a-c* because it is waiting for a voltage to be applied between pins 25 and 26 and/or between pins 30 and 31, yet the nurse call system is not applying any voltage between pins 25 and 26 or between pins 30 and 31 because it is waiting for patient support apparatus 20, 20*a* to implement its configuration settings. In such a situation, it is possible that patient support apparatus 20, 20*a* does not implement configuration option 232*a-c* and that nurse call system 70 does not detect the presence of patient support apparatus 20, 20*a*. In order to avoid such a situation, patient support apparatus 20*a* includes option 232*e*.

If the user selects the force interlocks option 232*e* (FIG. 12), controller 112 (for patient support apparatuses 20) or controller 184 (for patient support apparatuses 20*a*) is adapted to change configuration circuitry 132 without waiting to detect any voltage between pins of communication outlet 64. Instead, when option 232*e* is selected (along with one of options 232*a-c*), controller 112, 184 automatically electrically shorts together the pins identified in options 232*a,* 232b, or 232*c* without waiting to detect any voltage from the nurse call system 70. This avoids the stalemate situation mentioned above where patient support apparatus 20, 20*a* may be waiting to detect voltage from the nurse call system 70 before it applies its configuration settings while the nurse call system 70 may be waiting for the patient support apparatus 20, 20*a* to apply it configuration settings before it applies a voltage to communication outlet 64.

If the user selects the "disable digital volume" option 232*d* (FIG. 12), controller 112 (for patient support apparatuses 20) or controller 184 (for patient support apparatuses 20*a*) is adapted to not send a signal to television 72 to change its volume in response to a user activating control 50*l* or 50*m* (FIG. 3). Instead, patient support apparatus 20, 20*a* changes the amplification of its own onboard amplifier in response to the user activating control 50*l* or 50*m*. If the user does not select the “disable digital volume” option 232d, patient support apparatus 20, 20*a* sends a command to television 72 requesting it to increase or decrease its volume in response to a user activing controls 501 and/or 50*m*

Figure 13:
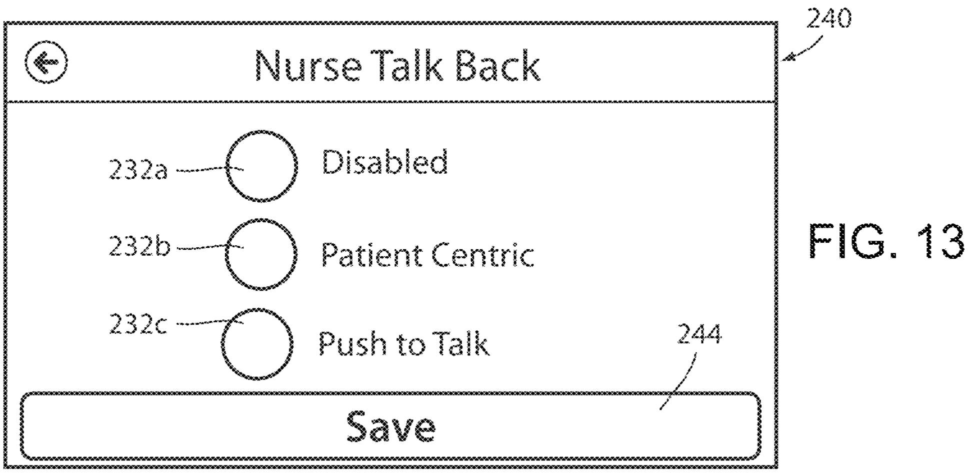
FIG. 13 is an illustrative nurse talk back screen displayable on the display of any of the patient support apparatuses disclosed herein or a display of any of the off-board electronic devices disclosed herein.

If a user selects nurse talk back option 202*d* of master configuration control screen 200 (FIG. 9), display 52 of control panel 54*a* displays a nurse talk back control screen 240, such as shown in FIG. 13. Nurse talk back control screen 240 includes a plurality of setting options 242*a-c* that are useful for managing the audio communications between the remote nurse and the patient. For many nurse call systems, the audio communication between the patient and the nurse takes place over a half-duplex communication channel. In such systems, only one person is able to speak at a time. For still other nurse call systems, no audio communications are able to take place, but the patient is able to send an electronic request to the nurse call system requesting that a nurse come and visit.

For those systems that utilize half-duplex communications, the audio signals from the patient's or the nurse's voice are sent over a single channel (e.g. pins 8 and pin 9), and the nurse call system typically determines whether the channel is being used to transmit audio signals from the nurse to the patient, or when the single channel is being used to transmit audio signals from the patient to the nurse.

If the user selects the “disabled” option 242*a* (FIG. 13), controller 112 (for patient support apparatuses 20) or controller 184 (for patient support apparatuses 20*a*) is adapted to not send any audio signals of the patient's voice to the nurse call system 70. Instead, headwall interface 120 sends a request for a nurse in response to the patient pressing control 50*g*. Any audio signals of the patient that are detected by microphone 176 are not forwarded by headwall interface 120 to communications outlet 64.

If the user selects the patient centric option 242b, controller 112 (for patient support apparatuses 20) or controller 184 (for patient support apparatuses 20*a*) is adapted to apply audio signals to the half-duplex communication channel (e.g. pins 8 and 9) whenever patient support apparatus 20, 20*a* detects that the patient is speaking into microphone 176. If the user selects the push to talk option 242c, controller 112 (for patient support apparatuses 20) or controller 184 (for patient support apparatuses 20*a*) is adapted to apply audio signals to the half-duplex communication channel only when the patient physically activates a control (not shown) on patient support apparatus 20, 20*a* necessary for him/her to communicate with the remote nurse. The control may be a button, switch, dial, or the like, that, when pressed, causes the patient's audio signals to be electrically applied to the half-duplex communication channel. The manner in which control system 98, 98*a* does or does not transfer audio signals of the patient's voice from microphone 176 to the communication channel is therefore dictated by the nurse talk back settings 242*a-c* of FIG. 13.

Figure 14:
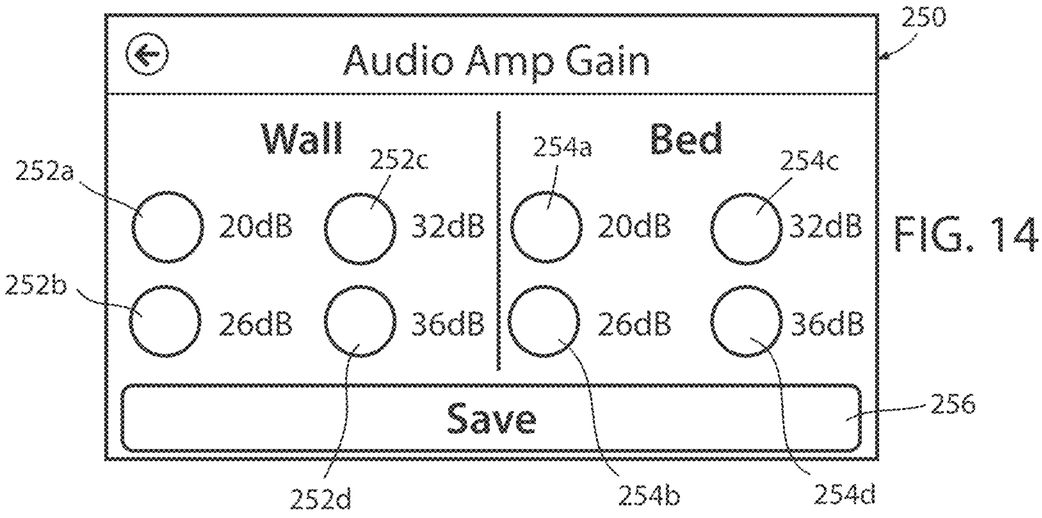
FIG. 14 is an illustrative audio gain screen displayable on the display of any of the patient support apparatuses disclosed herein or a display of any of the off-board electronic devices disclosed herein.

If a user selects audio amp gain option 202*e* of master configuration control screen 200 (FIG. 9), display 52 of control panel 54*a* displays an audio amp gain control screen 250, such as shown in FIG. 14. Audio amp gain control screen 250 includes a plurality of wall setting options 252*a-d* and a plurality of patient support apparatus 20, 20*a* setting options 254*a-d*. The wall settings 252a-d control the amount of amplification that headwall module 144 applies to the audio signals sent between communications outlet 64 and patient support apparatus 20, 20*a*. The patient support apparatus settings 254*a-d* control the amount of amplification that patient support apparatus 20, 20*a* applies to the audio signals sent between patient support apparatus 20 and communications outlet 64 (or between patient support apparatus 20*a* and headwall module 144, 144*a*. As can be seen in FIG. 14, the setting options includes selections for gains of 20 decibels (dB), 26 dB, 32 dB, and 36 dB.

In some embodiments, the gains shown in FIG. 14 refer to the amplification of the audio signals received from nurse call system 70, which are the voice signals received from the remotely positioned nurse (via a specific pin of communications outlet 64). In other embodiments, the gains shown in FIG. 14 refer to the amplification of the audio signals received from the television 72 (via a different pin of communications outlet 64). In still other embodiments, the gains shown in FIG. 14 refer to the amplification of both the audio signals received from nurse call system 70 as well as the audio signals received from television 72. In still other embodiments, patient support apparatuses 20, 20*a* may include settings allowing the user to separately control the gains for the television audio signals and the nurse call system audio signals received from communications outlet 64.

Figure 15:
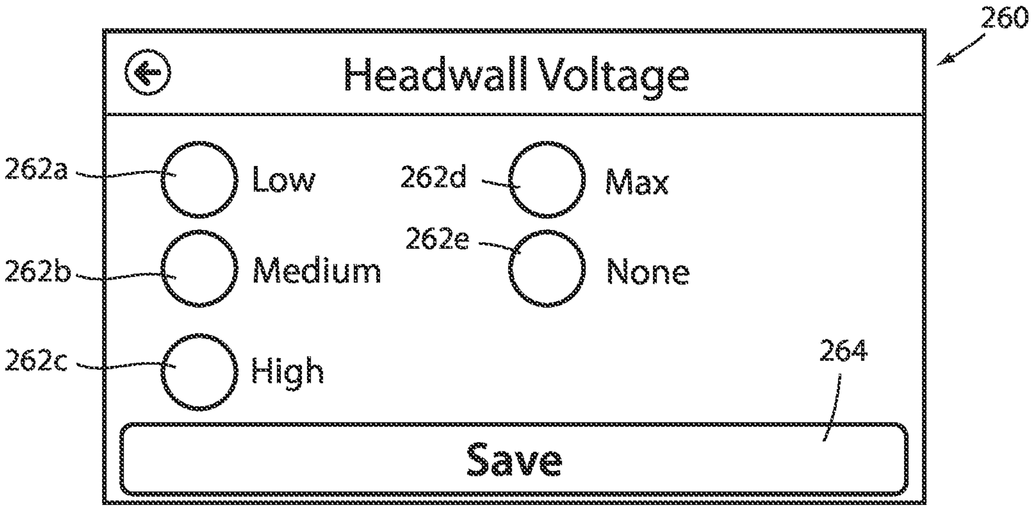
FIG. 15 is an illustrative headwall voltage screen displayable on the display of any of the patient support apparatuses disclosed herein or a display of any of the off-board electronic devices disclosed herein.

If a user selects headwall voltage option 202f of master configuration control screen 200 (FIG. 9), display 52 of control panel 54*a* displays a headwall voltage control screen 260, such as shown in FIG. 15. Headwall voltage control screen 260 includes a plurality of voltage options 262*a-e*. Voltage options 262*a-e* control how headwall module 144, 144*a* or patient support apparatus 20, 20*a* interprets the voltages applied by the nurse call system 70 between pins 16 and 29 and between pins 19 and 28. These voltages are used by patient support apparatus 20 to control the operation of nurse answer light 114 and nurse call lights 116, respectively.

Different nurse call systems 70 apply different voltages between pins 16 and 29 when a remotely positioned nurse answers a patient's call from patient support apparatus 20, 20*a*. Similarly, different nurse call system 70 apply different voltages between pins 19 and 28 when a nurse call is placed. In order for patient support apparatus 20, 20*a* to know when to illuminate lights 114 and 116, it must be configured to recognize what voltages are applied by nurse call system 70 between these two pairs of pins when a nurse answers a call and when a patient places a call, and what voltages might otherwise be present on these pins but not indicative of either a nurse answer or a patient call. Headwall voltage control screen 260 allows a user to tell patient support apparatus 20 what voltage levels on these pins should be interpreted as indicating that a nurse answered a call and what voltage levels should be interpreted as the nurse call system acknowledging that a patient has placed a call to a nurse (and these, in turn, tell patient support apparatus 20, 20*a* when to illuminate lights 114 and 116). At whatever voltage level the user selects, patient support apparatus 20, 20*a* is configured to illuminate lights 114 and 116 if the voltage exceeds the selected voltage, but to ignore (i.e. not turn on lights 114 and 116) if voltage is present between these pins but it does not exceed the configured voltage.

If the user selects “low voltage” option 262*a* of screen 260, controller 112 (for patient support apparatuses 20) or controller 184 (for patient support apparatuses 20*a*) illuminates nurse answer light 114 if the voltage between pins 16 and 29 exceeds the voltage corresponding to the “low voltage" of option 262*a*, and controllers 112, 184 illuminate nurse call light 116 if the voltage between pins 19 and 28 exceeds the voltage corresponding to the "low voltage" of option 262*a*. If the user selects "medium voltage" option 262*b* of screen 260, controller 112 (for patient support apparatuses 20) or controller 184 (for patient support apparatuses 20*a*) does the same thing, but only if the voltage exceeds the "medium voltage" option 262*b*. That is, controller 112, 184 illuminate nurse answer light 114 if the voltage between pins 16 and 29 exceeds the voltage corresponding to the "medium voltage" of option 262*b*, and controllers 112, 184 illuminate nurse call light 116 if the voltage between pins 19 and 28 exceeds the voltage corresponding to the "medium voltage" of option 262*b*. If the user selects "high voltage" option 262*c* or "max voltage" option 262*d* of screen 260, controller 112, 184 illuminates lights 114 and 116 in the same manner, but only if the voltage between the aforementioned pins exceeds a high or maximum level. Finally, if the user selects the "none" option 262*e* of screen 260, controller 112, 184 illuminates lights 114 and 116 if any non-zero voltage is detected between the aforementioned pins.

Although the specific numerical voltage levels that correspond to the low, medium, high, and max options 262*a-d* of FIG. 15 may vary, in some embodiments, the "low" option refers to three volts, the "medium" option refers to ten volts, the "high" option refers to twenty-five volts, and the "max" option refers to thirty-two volts. Other voltage levels, of course, may be used. Further, in some embodiments, headwall voltage control screen 260 may be modified to allow a user to input a specific numeric value, instead of, or in addition to, choosing one of the predefined voltage options 262*a-e*.

Each of controls screens 210, 220, 230, 240, 250, and 260 includes a "save" option 214, 224, 234, 244, 256, and 264, respectively. When the user activates these save options, headwall communications controller 112 stores the configuration option(s) selected by the user in a memory onboard patient support apparatus 20, 20*a*. If patient support apparatus 20, 20*a* is in communication with communications outlet 64 via nurse call cable 66, headwall communications controller 112 uses these saved configuration settings when communicating with communications outlet 64. If patient support apparatus 20*a* is wirelessly communicating with communications outlet 64 via headwall module 144, 144*a*, patient support apparatus 20*a* transmits the saved configuration settings to headwall module 144, 144*a*, and headwall module controller 184 saves these configuration settings in a memory onboard headwall module 144, 144*a*. Headwall module controller 184 thereafter uses these saved settings when communicating with communications outlet 64.

Patient support apparatus 20*a* is configured, in some embodiments, to act as a communications interface for headwall modules 144, 144*a*. That is, any changes to be made to the configuration of headwall modules 144, 144*a* are implemented via patient support apparatus 20*a*. Such changes may be implemented by changing any of the selected options on control screens 210, 220, 230, 240, 250, and/or 260, which are then stored in the memory of patient support apparatus 20, 20*a* and also transmitted to whichever headwall module 144, 144*a* the patient support apparatus 20*a* is in communication with (if any). Also, as previously noted, such configuration changes may be made using an electronic device 94 executing remote control application 140. Remote control application 140, in some embodiments, displays screens similar to, or the same as, screens 210, 220, 230, 240, 250, and/or 260 on the display of devices 94 and thereby allows the user to select the configuration options shown on these screens. When remote control application 140 displays such configuration options on the screen of an electronic device 94, it may also display a room number, a patient support apparatus 20, 20*a* identifier, and/or a headwall module 144, 144*a* identifier that specifies which patient support apparatus 20, 20*a* and/or which headwall module 144, 144*a* the configuration settings are to be applied to. The new settings are then sent by remote control application 140 to the patient support apparatus 20, 20*a*. Patient support apparatus 20*a* then shares the new settings with whichever headwall module 144, 144*a* it is in communication with, if any.

In some embodiments, when headwall module 144, 144*a* is first installed in a healthcare facility, it does not include any configuration settings stored in its memory. In such embodiments, headwall module 144, 144*a* may be programmed to automatically request these configuration settings from the first patient support apparatus 20*a* it successfully establishes a communications link with. If the patient support apparatus 20*a* does not include any stored settings in its memory to transfer to headwall module 144, 144*a*, it may be configured to display an error message on display 52 indicating to the user that headwall module 144, 144*a* and/or patient support apparatus 20*a* need to be configured in order to communicate with room devices 72, 74, 78 and/or nurse call system 70.

Once a headwall module 144, 144*a* receives a complete set of configuration settings from a patient support apparatus 20*a*, it does not thereafter request such configuration settings from a patient support apparatus 20*a*, even if a new patient support apparatus 20*a* is moved into communication with the headwall module 144, 144*a*. Instead, it continues to use the configuration settings it received, regardless of which patient support apparatus 20*a* it is currently in communication with. In some embodiments, headwall modules 144, 144*a* are configured to update their configuration settings only if a connected patient support apparatus 20*a* sends a command to change its configuration settings. In some embodiments, patient support apparatus 20*a* is configured to automatically send such a command to whichever headwall module 144, 144*a* it is currently in communication with if the user enters any new configuration settings while the patient support apparatus 20*a* is communicating with the headwall module 144, 144*a*. If patient support apparatus 20*a* is not currently communicatively linked to any headwall module 144, 144*a*, it does not send such configuration data until it later links to a headwall module 144, 144*a* and the user manually prompts patient support apparatus 20*a* to send the new configuration data.

Once a headwall module 144, 144*a* is configured with a complete set of configuration settings, it is programmed in some embodiments to automatically send a copy of those configuration settings to whichever patient support apparatus 20*a* that links with headwall module 144, 144*a*. (Headwall modules 144, 144*a* are programmed, in some embodiments, to only link to a single, adjacent patient support apparatus 20*a*). The patient support apparatus 20*a* then displays those settings on display 52 (in response to a user navigating to one or more settings screens) and the user is free to edit them, if desired.

Although patient support apparatus 20*a* may contain its own set of configuration settings stored in its memory, it does not use those settings, in at least one embodiment, unless it links to a headwall module 144, 144*a* that does not have any configuration settings stored thereon (in which case patient support apparatus 20*a* sends its configuration settings to the unconfigured headwall module 144, 144*a*). The reason that patient support apparatus 20*a* does use any configuration settings it contains in its onboard memory is because it relies on headwall modules 144, 144*a* to contain the correct set of configuration settings for the particular communications outlet 64 to which the headwall module 144, 144*a* is associated. This allows the patient support apparatus 20*a* to be moved to different locations in the healthcare facility without having to change any settings on the patient support apparatus 20*a*. Instead, the patient support apparatus 20*a* simply uses the configuration settings that are stored in the headwall module 144, 144*a* to which it is communicatively coupled.

In other words, every time a patient support apparatus 20*a* is moved to a different room, and/or some other location, having a different headwall module 144, 144*a* that may contain different configuration data, the patient support apparatus 20*a* does not need to be manually changed in any manner in order for it to successfully communicate with the specific communications outlet 64 that that particular headwall module 144, 144*a* is coupled to. Instead, because the headwall modules 144, 144*a* are all configured for the specific communications outlet 64 to which they are coupled (and the room devices 72, 74, 78 and nurse call system 70 coupled thereto), the patient support apparatus 20*a* that communicates with that headwall module 144, 144*a* does not need to change any of its communication protocols in order to correctly communicate with room devices 72, 74, 78 and/or nurse call system 70.

By retaining the configuration data for a particular set of room devices 72, 74, 78 and/or nurse call system 70 in a headwall module 144, 144*a* positioned within a particular room, patient support apparatus 20*a* can, in some embodiments, be programmed to communicate with all headwall modules 144, 144*a* in the same manner, regardless of whether the headwall modules 144, 144*a* are coupled to different brands of nurse call systems and/or regardless of whether they are coupled to different brands or types of room devices 72, 74, and/or 78. This avoids the need for the patient support apparatuses 20*a* to be changed each time they are moved to a different room, or other location, having different room devices 72, 74, 78 and/or a different nurse call system 70 installed. Instead, patient support apparatus 20a communicates with the associated headwall module 144, 144*a* in the same manner and allows the headwall module 144, 144*a* to "convert" those communications to the proper format for conveying to headwall communications outlet 64.

In some embodiments, patient support apparatus 20*a* may be configured to not store its own set of configuration settings data, but instead transfer any changes or data that are input via any of the control screens of FIGS. 10-15 to the associated headwall module 144, 144*a* without retaining such data in its own onboard memory. This includes any configuration settings that are set or edited via remote control application 140. Such remotely entered or edited configuration settings are passed to patient support apparatus 20*a*, which forwards them to its associated headwall module 144, 144*a* without saving them.

In at least one alternative embodiment, patient support apparatus 20*a* is configured to communicate with headwall module 144, 144*a* in a different manner depending upon how the headwall module 144, 144*a* is configured. Specifically, in this alternative embodiment, if headwall module 144, 144*a* has been configured to communicate with television 72 via the "traditional" option 212*e* of FIG. 10, patient support apparatus 20*a* is configured to send the same command to the headwall module 144, 144*a* in response to the user activating any of controls 50*l*-50*r*. The selected command may be a command that utilizes little bandwidth, thereby leaving more bandwidth for other communications between headwall module 144, 144*a* and patient support apparatus 20*a*. In still other embodiments, as mentioned above, patient support apparatus 20*a* may be configured to communicate with its associated headwall module 144, 144*a* in the same manner, regardless of how the associated headwall module 144, 144*a* is configured.

In summary, when an unconfigured headwall module 144, 144*a* communicatively coupled to a patient support apparatus 20*a*, it requests a set of configuration data from the patient support apparatus 20*a* and stores it in its own memory. Headwall module 144, 144*a* thereafter uses this stored configuration data when communicating with its associated communications outlet 64, and continues to use this configuration data unless it receives a command to change the configuration data from patient support apparatus 20*a* (which may originate from patient support apparatus 20 itself, or from remote control application 140). When a configured headwall module 144, 144*a* establishes communication with a patient support apparatus 20*a*, the headwall module 144, 144*a*, sends its configuration data to the patient support apparatus 20*a* so that the data can be displayed to the user and/or edited. However, unless the user manually changes the configuration data, the configured headwall module 144, 144*a* will continue to use its configuration data for its communications with communication outlet 64.

For both patient support apparatuses 20, 20*a* and headwall modules 144, 144*a*, the configuration data is used by configuration circuitry 132 to ensure proper communication with the associated communications outlet 64. When any changes are made to the configuration data, the configuration circuitry 132 automatically makes corresponding changes, as necessary, via software. Thus, there is no need for a user to manually change any dipswitches, or make any other physical changes, to the configuration circuitry 132 when the configuration data is changed. In this manner, both patent support apparatuses 20, 20*a* and headwall modules 144, 144*a* can be configured using control panels on patient support apparatus 20, 20*a* and/or electronic devices 94 without having to take any physical actions other than selecting the desired settings on these control panels.

Patient support apparatus 20, 20*a* is configured to display its current configuration settings data on display 52 in response to a user navigating to an appropriate set of screens. This may be done via the screens shown in FIGS. 10-15. In other words, although FIGS. 10-15 show a plurality of options that are all illustrated in the drawings as being unselected, it will be understood that, patient support apparatus 20, 20*a* is configured to show which options were previously checked (if patient support apparatus 20, 20*a* was previously configured or previously used to configure a headwall module 144, 144*a*). Thus, the control screens of FIGS. 10-15 are not only used to change configuration settings, but also to view the current configuration settings.

In some embodiments, patient support apparatus 20*a* is configured to display the configuration settings on the screens of FIGS. 10-15 in different manners, depending upon whether patient support apparatus 20*a* is currently communicating with a headwall module 144, 144*a* or not. In such embodiments, if patient support apparatus 20*a* is currently in communication with a headwall module 144, 144*a* and the user navigates to any of the screens of FIGS. 10-15, patient support apparatus 20*a* displays the configuration settings thereon that are stored in the memory of the headwall module 144, 144*a* (if any) that it is currently in communication with (it displays this data after receiving it and/or requesting it from the headwall module 144, 144*a*). Further, in such embodiments, if patient support apparatus 20*a* is currently not in communication with a headwall module 144, 144*a* and the user navigates to any of the screens of FIGS. 10-15, patient support apparatus 20*a* displays the configuration settings (if any) that it has stored in its own onboard memory. Thus, in these embodiments, patient support apparatus 20*a* is configured to automatically always display the configuration settings of any headwall module 144, 144*a* it is in communication with, and to only display any configuration settings stored on the patient support apparatus 20, 20*a* if it is not currently in communication with a headwall module 144, 144*a*. In some of these embodiments, patient support apparatus 20*a* may include a control for allowing the user to see both the configuration settings of the headwall module 144, 144*a* and the patient support apparatus 20*a* regardless of whether or not the patient support apparatus 20 is communicating with a headwall module 144, 144*a* or not.

In some embodiments, headwall modules 144, 144*a* are constructed to include any or all of the functionality of the wireless headwall units disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:

a frame;

a support surface adapted to support a patient thereon;

a first wireless transceiver adapted to communicate with a headwall module attached to a headwall of a healthcare facility at a fixed location, the headwall module adapted to be electrically coupled to an outlet on the headwall, the outlet including at least one pin in electrical communication with a room device positioned within a room in which the patient support apparatus is located;

a second wireless transceiver adapted to communicate with a server hosted on a local area network of the healthcare facility, the second wireless transceiver adapted to communicate with the server via a wireless access point of the local area network;

a room control adapted to be activated by the patient, the room control adapted to control a feature of the room device; and a controller adapted to transmit a room control signal to the headwall module via the first wireless transceiver in response to a user activating the room control on the patient support apparatus, the controller further adapted to receive a room control command from an off-board source via the second wireless transceiver and to transmit the room control signal to the headwall module via the first wireless transceiver in response to receiving the room control command, wherein the headwall module is adapted to forward the room control signal to the room device to thereby allow the room device to be controlled both by the room control and by the off-board source, wherein the patient support apparatus is adapted to act as communication intermediary for enabling the off-board source to remotely control the feature of the room device.

2. The patient support apparatus of claim 1 wherein the room device is one of a room light positioned in the room or a television positioned in the room, and the feature of the room device is one of an on/off state of the room light or at least one of a channel or volume of the television.

3. The patient support apparatus of claim 2 wherein the controller is adapted to receive room configuration data from the off-board source via the second wireless transceiver, the room configuration data including voltage data specifying a voltage level to apply to the pin in order to control the television.

4. The patient support apparatus of claim 2 further comprising:

a headwall interface adapted to couple to a cable having a plurality of electrical conductors, a first one of the electrical conductors adapted to be in electrical communication with the pin when a cable is coupled to the outlet instead of the headwall module; and wherein the controller is further adapted to automatically retrieve from the headwall module room configuration data, the room configuration data including voltage data specifying a voltage level to apply to the pin in order to control the television, wherein the controller is further adapted to use the voltage data to control the television when the cable is coupled to the outlet and the patient activates the room control.

5. The patient support apparatus of claim 1 wherein the controller is further adapted to receive a room control schedule from the off-board source and to use the room control schedule to automatically control the feature of the room device according to the room control schedule.

6. The patient support apparatus of claim 1 further comprising an exit detection system adapted to detect when the patient exits from the support surface and to issue an exit alert in response thereto, wherein the outlet further includes multiple pins in communication with a nurse call system and the controller is further adapted to receive nurse call configuration data from the off-board source via the second wireless transceiver and to forward the nurse call configuration data to the headwall module via the first wireless transceiver, the nurse call configuration data indicating which pin of the multiple pins is to be used to communicate the exit alert to the nurse call system.

7. The patient support apparatus of claim 1 wherein the first wireless transceiver is adapted to operate in accordance with standard IEEE 802.14.1 and the second wireless transceiver is a WiFi transceiver, and the off-board source is one of a smart phone, a tablet computer, or a laptop computer in communication with the server.

8. A patient support apparatus comprising:

a frame;

a support surface adapted to support a patient thereon;

a first wireless transceiver adapted to communicate with a headwall module attached to a headwall of a healthcare facility at a fixed location, the headwall module adapted to be electrically coupled to an outlet on the headwall, the outlet including at least one pin in electrical communication with a room device positioned within a room in which the patient support apparatus is located;

a second wireless transceiver adapted to communicate with a server hosted on a local area network of the healthcare facility, the second wireless transceiver adapted to communicate with the server via a wireless access point of the local area network, the second wireless transceiver adapted to receive a room control schedule from an off-board source, the room control schedule identifying a time window;

a room control adapted to be activated by the patient, the room control adapted to control a feature of the room device; and a controller adapted to perform the following:

transmit a room control signal to the headwall module via the first wireless transceiver in response to a user activating the room control on the patient support apparatus at times outside of the time window;

forward the room control schedule to the headwall module via the first wireless transceiver;

instruct the headwall module to send control signals to the room device according to the room control schedule; and at times inside of the time window, override the room control such that the controller does not transmit the room control signal to the headwall module via the first wireless transceiver in response to the user activating the room control on the patient support apparatus.

9. The patient support apparatus of claim 8 wherein the room device is a room light positioned in the room, the feature of the room device is an on/off state of the room light, and the room control schedule includes at least one of automatically turning on or off the room light at a specified time.

10. The patient support apparatus of claim 8 wherein the room device is a television positioned in the room, the feature of the room device is at least one of a channel or a volume of the television, and the room control schedule includes at least one of turning off the television at a specified time or limiting a volume of the television at a specified time.

11. The patient support apparatus of claim 8 wherein the first wireless transceiver is adapted to operate in accordance with standard IEEE 802.14.1 and the second wireless transceiver is a WiFi transceiver, and the off-board source is one of a smart phone, a tablet computer, or a laptop computer in communication with the server.

12. A patient support apparatus comprising:

a frame;

a support surface adapted to support a patient thereon;

a first wireless transceiver adapted to communicate with a headwall module attached to a headwall of a healthcare facility at a fixed location, the headwall module adapted to be electrically coupled to an outlet on the headwall, the outlet including at least one pin in electrical communication with a room device positioned within a room in which the patient support apparatus is located;

a second wireless transceiver adapted to communicate with a server hosted on a local area network of the healthcare facility, the second wireless transceiver adapted to communicate with the server via a wireless access point of the local area network;

a room control adapted to be activated by the patient, the room control adapted to control a feature of the room device; and a controller adapted to perform the following:

transmit a room control signal to the headwall module via the first wireless transceiver in response to a user activating the room control on the patient support apparatus;

receive room configuration data from an off-board source via the second wireless transceiver, the room configuration data including voltage data specifying a voltage level the headwall module is to apply to the pin in order to control the room device;

forward the room configuration data to the headwall module via the first wireless transceiver;

instruct the headwall module to use the room configuration data to control the voltage level applied to the pin when controlling the feature of the room device;

request a copy of the room configuration data from the headwall module when the patient support apparatus first establishes a communication link with the headwall module;

display the copy on a display of the patient support apparatus;

allow a user to modify the copy; and transmit back to the headwall module the modified copy of the room configuration data.

13. The patient support apparatus of claim 12 further comprising an exit detection system adapted to detect when the patient exits from the support surface and to issue an exit alert in response thereto, wherein the outlet further includes multiple pins in communication with a nurse call system and the controller is further adapted to receive nurse call configuration data from the off-board source via the second wireless transceiver and to forward the nurse call configuration data to the headwall module via the first wireless transceiver, the nurse call configuration data indicating which pin of the multiple pins is to be used to communicate the exit alert to the nurse call system.

14. The patient support apparatus of claim 12 wherein the room device is a television positioned in the room, the feature of the room device is at least one of a channel or a volume of the television, and the patient support apparatus further comprises:

a headwall interface adapted to couple to a cable having a plurality of electrical conductors, a first one of the electrical conductors adapted to be in electrical communication with the pin when a cable is coupled to the outlet instead of the headwall module; and wherein the controller is further adapted to automatically retrieve from the headwall module room configuration data, the room configuration data including voltage data specifying the voltage level to apply to the pin in order to control the television, wherein the controller is further adapted to use the voltage data to control the television when the cable is coupled to the outlet and the patient activates the room control.

15. The patient support apparatus of claim 12 wherein the controller is further adapted to receive a room control command from the off-board source via the second wireless transceiver and to transmit the room control signal to the headwall module via the first wireless transceiver in response to receiving the room control command, wherein the headwall module is adapted to forward the room control signal to the room device to thereby allow the room device to be controlled both by the room control and by the off-board source.

16. The patient support apparatus of claim 12 further comprising a viewing control adapted to be activated by the user, wherein the controller is adapted to perform the following: (a) when the patient support apparatus is communicatively coupled to the headwall module, to retrieve the room configuration data from the headwall module in response to a user activating the viewing control and to display the retrieved room configuration data on a display of the patient support apparatus; and (b) when the patient support apparatus is not communicatively coupled to the headwall module, to retrieve a set of configuration data from a memory onboard the patient support apparatus in response to the user activating the viewing control and to display the set of configuration data on the display.

* * * * *